(12) United States Patent
Vasiev et al.

(10) Patent No.: US 12,377,224 B1
(45) Date of Patent: Aug. 5, 2025

(54) HOLD ASSISTANCE DEVICE FOR USE WITH A MEDICAMENT DELIVERY DEVICE

(71) Applicant: Genzyme Corporation, Cambridge, MA (US)

(72) Inventors: Iskandar Vasiev, Melbourn (GB); Kiara May-Leen Taylor, Cambridge (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/984,427

(22) Filed: Dec. 17, 2024

(51) Int. Cl.
*A61M 5/315* (2006.01)

(52) U.S. Cl.
CPC .... *A61M 5/31571* (2013.01); *A61M 5/31515* (2013.01)

(58) Field of Classification Search
CPC .......... A61M 5/31571; A61M 5/31515; A61M 5/31566; A61M 5/31576; A61M 5/31573; A61M 5/31513; A61M 5/30; A61M 5/178; A61M 2209/084; A61M 2209/088
See application file for complete search history.

(56) References Cited

U.S. PATENT DOCUMENTS

2017/0361030 A1* 12/2017 Moore .................. A61M 5/326
2023/0355892 A1* 11/2023 Calderwood ....... A61M 5/3245

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

* cited by examiner

*Primary Examiner* — Tasnim Mehjabin Ahmed
(74) *Attorney, Agent, or Firm* — Fish & Richardson P.C.

(57) ABSTRACT

A hold assistance device for use with a medicament delivery device is described. The hold assistance device includes a body that includes: a receiving volume for receiving a medicament delivery device; a proximal portion comprising a proximal end of the body; a distal portion comprising a distal end of the body, the proximal and distal ends defining an axial direction; and a connecting portion arranged between the proximal and distal portions, wherein the connecting portion is configured to flex into the receiving volume in a direction generally normal to the axial direction, causing the proximal portion to move axially relative to the distal portion.

19 Claims, 8 Drawing Sheets

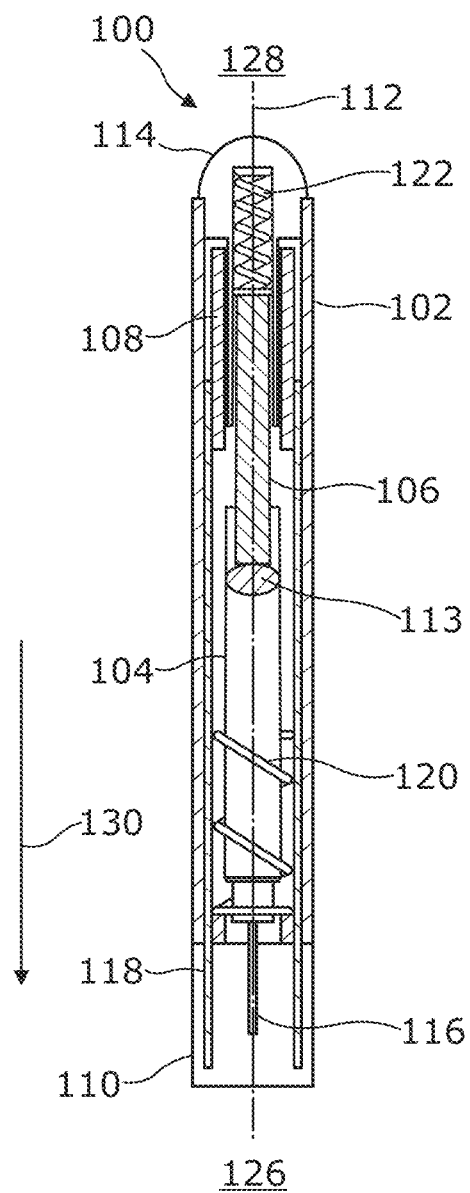
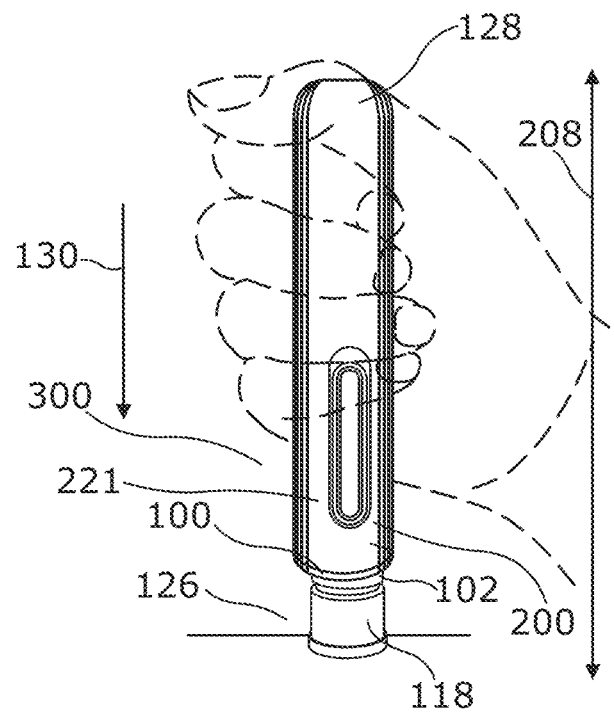
FIG. 1
FIG. 2

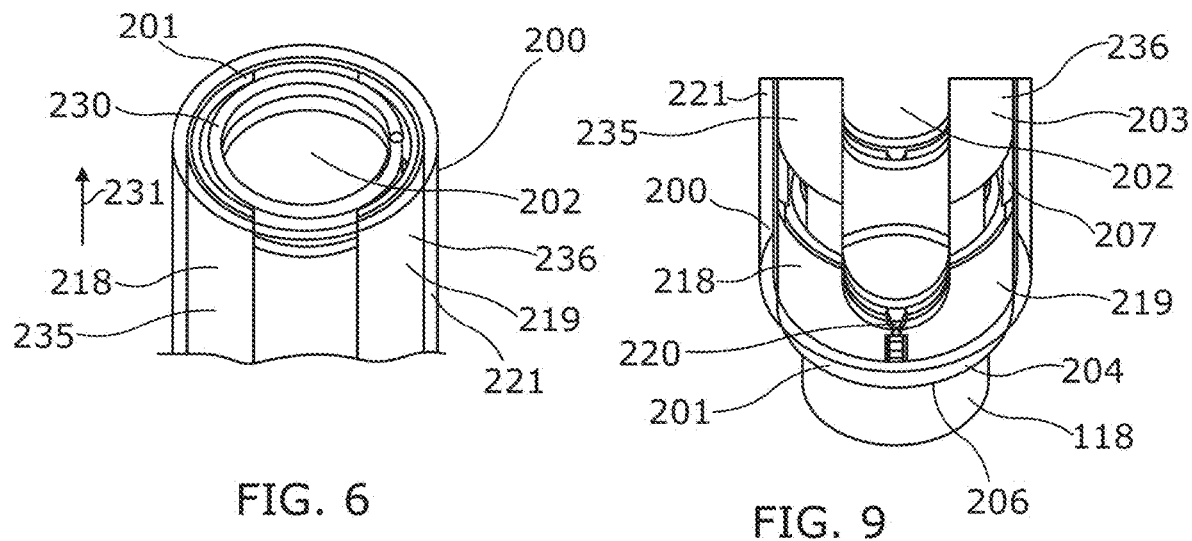
FIG. 6
FIG. 9
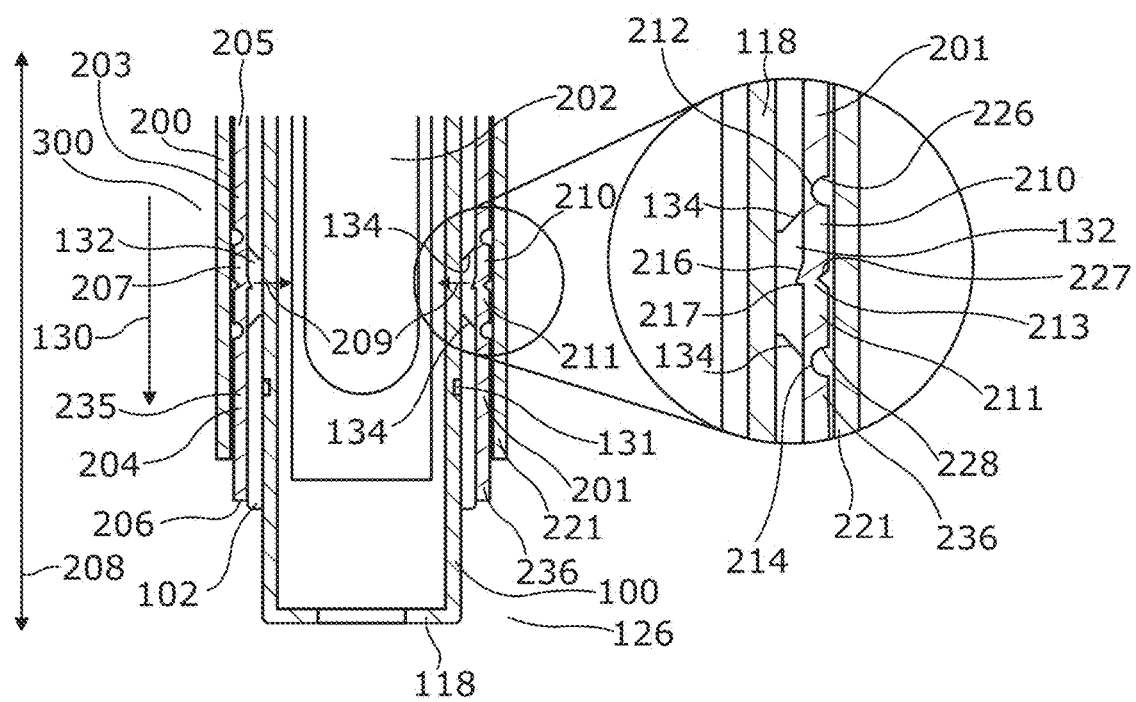
FIG. 7

HOLD ASSISTANCE DEVICE FOR USE WITH A MEDICAMENT DELIVERY DEVICE

TECHNICAL FIELD

The present disclosure relates to a hold assistance device for use with a medicament delivery device; to a medicament delivery system comprising a hold assistance device and a medicament delivery device; and to a method of operating a medicament delivery system.

BACKGROUND

Medicament delivery devices can be used to deliver a range of medicaments. In some devices, the device must be held in a holding position at an injection site to ensure that a correct dose of medicament is dispensed from the device, before removing the device from the injection site. It may be difficult to hold the device in the holding position whilst the medicament is dispensed. This may result in pain, discomfort, a wet injection site, early device removal and/or partial delivery of the medicament. Administering an injection is a process which presents several risks and challenges, both mental and physical.

SUMMARY

The present disclosure provides a hold assistance device to assist a user with the holding of a medicament delivery device in the holding position whilst the medicament is dispensed.

A first aspect of this disclosure provides a hold assistance device for use with a medicament delivery device, the hold assistance device comprising a body comprising: a receiving volume for receiving a medicament delivery device; a proximal portion comprising a proximal end of the body; a distal portion comprising a distal end of the body, the proximal and distal ends defining an axial direction; and a connecting portion arranged between the proximal and distal portions, wherein the connecting portion is configured to flex into the receiving volume in a direction generally normal to the axial direction, causing the proximal portion to move axially relative to the distal portion.

Optionally, the body is arrangeable in: a first position in which the connecting portion is in an unflexed state and the proximal portion is spaced apart from the distal portion along the axial direction by a first distance; and a second position in which the connecting portion is in a flexed state and the proximal portion is spaced apart from the distal portion along the axial direction by a second distance that is smaller than the first distance.

Optionally, the hold assistance device further comprises a body biasing member configured to bias the body towards the first position.

Optionally, the body biasing member comprises a spring, for example an extension spring.

Optionally, the body biasing member comprises a spring coupled to the proximal end of the body.

Optionally, the body biasing member comprises an extension spring; wherein when the body is in the first position, the extension spring is in a natural, unextended state; and when the body is in the second position, the extension spring is in an extended, stretched state.

Optionally, the body biasing member is configured to bias the body towards a proximal direction.

Optionally, the connecting portion is configured to flex into the receiving volume in a direction generally normal to the axial direction in a radially inwards direction.

Optionally, when the connecting portion is in a flexed state in which it is flexed into the receiving volume in a direction generally normal to the axial direction, the connecting portion is arranged to protrude into the receiving volume.

Optionally, along the axial direction, the connecting portion is arranged between the proximal and distal portions.

Optionally, the connecting portion is integrally formed with the proximal portion and the distal portion.

Optionally, the body is a moulded body moulded integrally to comprise the proximal portion, the distal portion and the connecting portion.

Optionally, the connecting portion comprises a linkage, such as a two bar linkage.

Optionally, the connecting portion comprises a hinge.

Optionally, the connecting portion comprises a knee joint or an elbow joint.

Optionally, the connecting portion comprises a first connecting portion arranged adjacent to the proximal portion, and a second connecting portion arranged adjacent to the distal portion, wherein the first connecting portion is hinged relative to the proximal portion by a first pivot point, the first connecting portion is hinged relative to the second connecting portion by a second pivot point, and the second connecting portion is hinged relative to the distal portion by a third pivot point.

Optionally, the connecting portion comprises one or more cut-outs, grooves, recesses or apertures.

Optionally, in the region of each of one or more cut-outs formed in the connecting portion, the connecting portion has a reduced thickness in a direction normal to the axial direction.

Optionally, the connecting portion is configured to be bent in the region of each of the one or more cut-outs.

Optionally, the connecting portion comprises one or more cut-outs each arranged to be generally normal to the axial direction.

Optionally, the connecting portion comprises one or more cut-outs, wherein each of the one or more cut-outs is generally a semicircular, a triangular, a pentagonal, a square, a rectangle, a quadrilateral, a rhombus, a parallelogram, a diamond, a hexagonal, or any other suitable curved or linear sided shape.

Optionally, the connecting portion comprises a first cut-out corresponding with the first pivot point, a second cut-out corresponding with the second pivot point, and a third cut-out corresponding with the third pivot point.

Optionally, the connecting portion comprises a first cut-out arranged between the proximal portion and the first connecting portion, a second cut-out arranged between the first connecting portion and the second connecting portion, and a third cut-out arranged between the second connecting portion and the distal portion.

Optionally, the second cut-out is arranged between the first and third cut-outs.

Optionally, the first cut-out and the third cut-out are each generally semicircular, and the second cut-out is generally pentagonal or triangular.

Optionally, the first connecting portion and the second connecting portion are approximately equal in length along the axial direction.

Optionally, the first connecting portion has a first length, and the second connecting portion has a second length, wherein the first length is different to the second length.

Optionally, the connecting portion is configured to flex into the receiving volume in a radial direction generally normal to the axial direction, such that when the connecting portion is in a flexed state, the first and second connecting portions are configured to be angled relative to the radial direction by an angle of between approximately 15° and 75°, preferably between approximately 45° and 75°, preferably between approximately 60° and 75°, preferably between approximately 70° and 75°.

Optionally, the connecting portion comprises a protruding portion arranged to protrude towards the receiving volume in a direction generally normal to the axial direction.

Optionally, the protruding portion is arranged approximately at the centre of the connecting portion along the axial direction.

Optionally, the protruding portion comprises a ramp comprising a surface that is inclined relative to the axial direction.

Optionally, the distal portion is configured to be coupled to a main body of a medicament delivery device and to remain fixed relative thereto, and the proximal portion is configured to be movable relative to the main body of the medicament delivery device along the axial direction.

Optionally, the body is generally cylindrical and is configured to circumscribe a medicament delivery device.

Optionally, the receiving volume is generally cylindrical.

Optionally, the body comprises a clamshell portion configured to receive and close around a medicament delivery device.

Optionally, the body is generally in the form of a clamshell configured to close around a medicament delivery device, for example to couple the hold assistance device thereto by closing therearound.

Optionally, the body comprises a first clamshell portion and a second clamshell portion.

Optionally, the first clamshell portion comprises a first half of the body and the second clamshell portion comprises a second half of the body, in a circumferential direction that is generally normal to the axial direction.

Optionally, the first clamshell portion is hingeably connected to the second clamshell portion.

Optionally, the first clamshell portion is hingeably integrally formed with the second clamshell portion.

Optionally, the body further comprises an interlock mechanism configured to couple the first and second clamshell portions together when the clamshell body is closed around a medicament delivery device.

Optionally, the interlock mechanism is further configured to couple the distal portion to a main body of a medicament delivery device.

Optionally, the interlock mechanism comprises a clip, a pin, and/or a snap fit or the like.

Optionally, the hold assistance device further comprises a housing arranged to circumscribe at least a portion of the body, wherein the proximal portion is configured to be movable relative to the housing along the axial direction.

Optionally, the housing is configured to slidably receive the body.

Optionally, the housing comprises an outer surface of the hold assistance device.

Optionally, the housing is generally cylindrical.

Optionally, the housing comprises a generally elongate sleeve.

Optionally, the housing is configured to be axially movable along the axial direction.

Optionally, the proximal portion of the body is configured to be movable relative to the housing.

Optionally, the housing is configured to be movable relative to the distal portion of the body.

Optionally, the body biasing member is configured to bias the body towards the first position relative to the housing.

Optionally, the body comprises one or more generally elongate arms, wherein each of the generally elongate arms comprises a respective proximal portion, a respective distal portion, and a respective connecting portion.

Optionally, the body comprises a plurality of generally elongate arms arranged to be equally spaced apart from one another around a circumferential direction of the hold assistance device.

Optionally, the body comprises two generally elongate arms arranged to be diametrically opposed to one another.

Optionally, the body is generally annular and comprises a proximal portion, a distal portion and a connecting portion which each extend around substantially the entire circumference of the hold assistance device.

A second aspect of this disclosure provides a medicament delivery system comprising the hold assistance device of the first aspect of this disclosure, and a medicament delivery device. The medicament delivery device comprises: a main body configured to receive a medicament cartridge and comprising a proximal end and a distal end; a needle for delivery of medicament from the medicament cartridge; a needle cover axially movable relative to the main body between: an extended position in which the needle cover extends from the distal end of the main body and covers a distal end of the needle which protrudes from the main body; and a retracted position in which the needle cover is arranged in a proximal position relative to the extended position such that the distal end of the needle protrudes from a distal end of the needle cover; and a needle cover biasing member configured to bias the needle cover axially in the distal direction towards the extended position. The distal portion of the body of the hold assistance device is configured to be coupled to the main body of the medicament delivery device, and the proximal portion of the body of the hold assistance device is configured to be movable relative to the main body of the medicament delivery device along the axial direction. When the hold assistance device is coupled to the medicament delivery device and the connecting portion is in a flexed state, the connecting portion is arranged to resist axial movement of the needle cover.

Optionally, the hold assistance device comprises one or more of the optional features recited above in relation to the first aspect of this disclosure.

Optionally, the medicament delivery system further comprises a medicament cartridge containing medicament.

Optionally, the needle cover biasing member comprises a spring, for example a compression spring.

Optionally, the needle cover biasing member comprises a compression spring; wherein when the needle cover is in the extended position the compression spring is in a natural, extended, uncompressed state; and when the needle cover is in the retracted position the compression spring is in a compressed state.

Optionally, when the connecting portion is in the flexed state, the hold assistance device is configured to provide an offsetting force which acts generally in an opposite direction to a biasing force exerted on the needle cover by the needle cover biasing member.

Optionally, when the connecting portion is in the flexed state, the connecting portion is arranged to resist movement of the needle cover from the retracted position towards the extended position.

Optionally, when the connecting portion is in the flexed state, the connecting portion is arranged to resist distal axial movement of the needle cover towards the extended position.

Optionally, when the connecting portion is in the flexed state, the connecting portion is arranged to at least partially obstruct axial movement of the needle cover.

Optionally, the main body comprises a first receiving element for receiving the connecting portion when the connecting portion is in a flexed state, such that when the hold assistance device is coupled to the medicament delivery device and the connecting portion is arranged in the flexed state, the connecting portion is configured to flex into the first receiving element to limit movement of the proximal portion of the body of the hold assistance device in the axial direction.

Optionally, the connecting portion is configured to flex towards a central region of the receiving volume via the first receiving element.

Optionally, the first receiving element comprises an aperture, a groove, a channel or a recess.

Optionally, when the connecting portion is in a flexed state, the first receiving element is configured to be axially aligned with the flexed connecting portion along the axial direction.

Optionally, when the connecting portion is in an unflexed state, the first receiving element is configured to be axially offset from the unflexed connecting portion along the axial direction, such that the first receiving element is only positioned to receive the connecting portion when the connecting portion is in the flexed state.

Optionally, the first receiving element comprises one or more first receiving element surfaces configured to bear against the connecting portion when the connecting portion is arranged in the flexed state, such that the one or more first receiving element surfaces are arranged to obstruct the connecting portion from moving in the axial direction.

Optionally, the first receiving element comprises two receiving element surfaces that are each arranged to be generally normal to the axial direction, and to be generally parallel to one another.

Optionally, the first receiving element comprises two receiving element surfaces that are each arranged to be angled relative to the axial direction.

Optionally, the needle cover comprises a second receiving element for receiving the connecting portion when the connecting portion is in a flexed state and the needle cover is in the retracted position, such that when the hold assistance device is coupled to the medicament delivery device and the needle cover is in the retracted position and the connecting portion is arranged in the flexed state, the connecting portion is configured to flex into the second receiving element to resist movement of the needle cover axially in the distal direction towards the extended position.

Optionally, the second receiving element comprises an aperture, a groove, a channel or a recess.

Optionally, when the connecting portion is in an unflexed state, the second receiving element is configured to be axially offset from the unflexed connecting portion along the axial direction, such that the second receiving element is only positioned to receive the connecting portion when the connecting portion is in the flexed state.

Optionally, along the axial direction, the first receiving element comprises a first spacing for receiving the flexed connecting portion, and the second receiving element comprises a second spacing for receiving the flexed connecting portion, wherein the first spacing is greater than the second spacing.

Optionally, when the connecting portion is in the flexed state, the connecting portion is configured to engage with a distal end portion of the needle cover, to apply a clamping force thereto, to resist axial movement of the needle cover.

Optionally, the body of the hold assistance device is arrangeable in: a first position in which the connecting portion is in an unflexed state and the proximal portion is spaced apart from the distal portion along the axial direction by a first distance; and a second position in which the connecting portion is in a flexed state and the proximal portion is spaced apart from the distal portion along the axial direction by a second distance that is smaller than the first distance; wherein when the needle cover is moved from the extended position to the retracted position, the body of the hold assistance device is caused to be moved from the first position into the second position.

Optionally, when the hold assistance device is coupled to the medicament delivery device, the medicament delivery system is arrangeable in a pre-activated position in which the needle cover is in the extended position and the body is in the first position such that the connecting portion is in an unflexed state.

Optionally, when the hold assistance device is coupled to the medicament delivery device, the medicament delivery system is arrangeable in an activated position in which the body is in the second position such that the connecting portion is in a flexed state and movement of the needle cover from the extended position to the retracted position causes the connecting portion to engage with the needle cover, such that when the connecting portion is engaged with the needle cover, the connecting portion is arranged to resist axial movement of the needle cover from the retracted position back towards the extended position.

Optionally, the connecting portion is configured to be moved from an unflexed state into the flexed state upon the application of a user applied force in the distal direction to the medicament delivery device.

Optionally, the connecting portion is configured to be moved from an unflexed state into the flexed state upon movement of the needle cover from the extended position towards the retracted position.

Optionally, the distal portion is configured to be coupled to the main body by a clip or a snap fit connection.

Optionally, the distal portion comprises a receiving element, for example an aperture, groove, recess or channel, which is configured to receive a corresponding protruding element of the main body in order to couple the distal portion to the main body.

Optionally, the protruding element of the main body is arranged to protrude in a generally radial direction that is generally normal to the axial direction.

Optionally, the protruding element of the main body comprises a ramp or wedge shape and comprises an inclined surface.

A third aspect of this disclosure provides a method of operating a medicament delivery system as in the second aspect of this disclosure, the method comprising: coupling the distal portion of the body of the hold assistance device to the main body of the medicament delivery device; moving the needle cover from the extended position to the retracted position; moving the body of the hold assistance device from a first position in which the connecting portion is in an unflexed state into a second position in which the connecting portion is in a flexed state and is arranged to protrude into the receiving volume, such that the connecting portion is arranged to resist axial movement of the needle cover from the retracted position to the extended position; and moving the body of the hold assistance device from the second position to the first position to cause the connecting portion to unflex such that it no longer protrudes into the receiving volume and the needle cover is free to move axially in the distal direction towards the extended position under a biasing force of the needle cover biasing member.

Optionally, the step of moving the needle cover from the extended position to the retracted position comprises placing the medicament delivery device against a surface, for example wherein the surface comprises the skin of a patient at an injection site, and applying a user applied downward force in the distal direction towards the surface, thus pushing the needle cover against the surface and causing it to be pushed inside the main body to retract thereinside.

Optionally, the step of moving the body of the hold assistance device from the first position into the second position occurs after the step of moving the needle cover from the extended position to the retracted position.

Optionally, the step of moving the body of the hold assistance device from the first position into the second position occurs simultaneously with the step of moving the needle cover from the extended position to the retracted position.

Optionally, the step of moving the needle cover from the extended position to the retracted position causes the body of the hold assistance to be automatically moved from the first position into the second position, which may occur simultaneously or subsequently.

Optionally, between the step of moving the body of the hold assistance device form the first position into the second position, and the step of moving the body of the hold assistance device from the second position to the first position to cause the connecting portion to unflex, the method further comprises holding the medicament delivery device for a required duration of time at an injection site of a patient.

Optionally, the step of holding the medicament delivery device for a required duration of time at an injection site of a patient comprises a user of the medicament delivery system holding the medicament delivery device at the injection site for an amount of time required for completion of delivery of a medicament from the needle to be complete.

Optionally, after the step of moving the body of the hold assistance device from the second position to the first position to cause the connecting portion to unflex, the method further comprises moving the needle cover from the retracted position back into the extended position.

Optionally, the step of moving the needle cover from the retracted position back into the extended position comprises moving the medicament delivery device away from an injection site of a patient.

Optionally, moving the medicament delivery device away from an injection site of a patient comprises moving the medicament delivery device in a proximal direction away from the skin of a patient, to remove a user hold force pushing the needle cover inside the housing as a result of pressing the needle cover against the skin of the patient, such that when the medicament delivery device is moved away from the skin, the needle cover is permitted to extend distally again under the action of a biasing force of the needle cover biasing member.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Embodiments will now be described, by way of example only, with reference to the accompanying drawings, in which:

FIG. 1 shows a cross-sectional schematic view of a medicament delivery device;

FIG. 2 shows a medicament delivery system;

FIG. 6 shows a medicament delivery system;

FIG. 7 shows a cross-sectional schematic view of a medicament delivery system, including an enlarged view of a portion thereof;

FIG. 9 shows a medicament delivery system;

DETAILED DESCRIPTION

Figure 3:
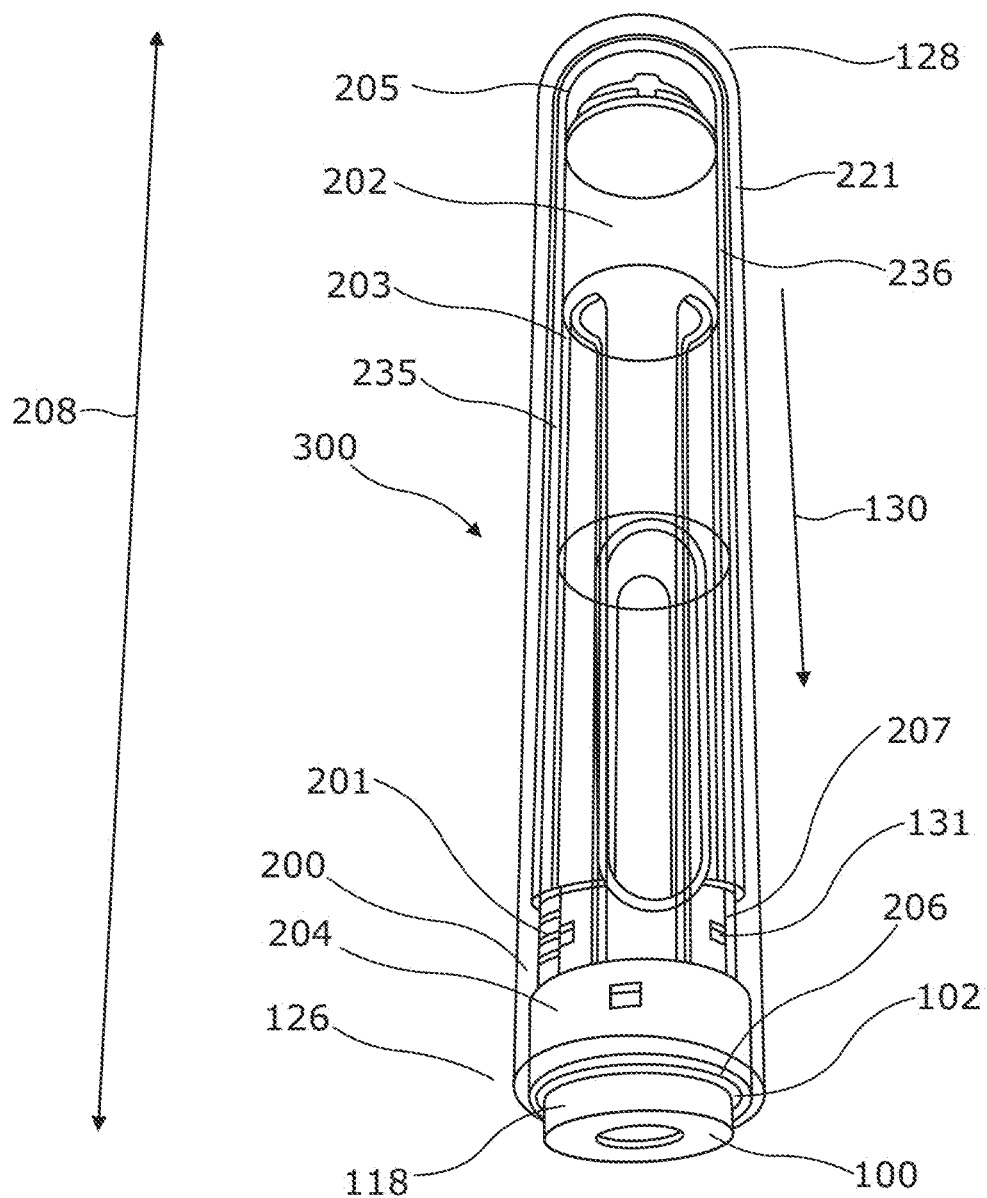
FIG. 3 shows a medicament delivery system.

A drug delivery device (also referred to as an injection device), as described herein, may be configured to inject a medicament into a subject such as a human or animal. For example, delivery could be sub-cutaneous, intra-muscular, or intravenous. Such a device could be operated by a user, who may or may not be the subject. In examples where the user is not the subject, the user may be a care-giver such as a nurse or physician. The device can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors require user actions to commence medicament delivery. One of these actions may involve a user placing a needle cover (also referred to as a needle shroud or needle sleeve) against an injection site of a subject and applying an axial force to the device to cause the needle cover to retract into the housing of the device. As the needle cover retracts into the housing, the needle of the device extends beyond the needle cover and penetrates the injection site of the subject (e.g. the subject's skin). Medicament delivery may be automatically initiated in response to the retraction of the needle cover or in response to some other action by the user, for example the user pressing a button on the device. Once medicament delivery has been initiated, a medicament delivery mechanism will cause medicament contained within the device to be injected into the subject via the needle. The user should hold the device steady with respect to the injection site during the course of medicament delivery to ensure the needle remains steady within the subject. This is to minimise pain and/or discomfort for the subject, and to prevent a wet injection site, early device removal and/or partial medicament delivery.

After the device is removed from injection site, many autoinjectors cover the needle with the needle cover/needle shroud, which is extended out of the device by a control spring. During activation of the device and while holding the device steady during medicament delivery, the user must counteract the biasing force applied by the control spring to the needle cover. However, some users such as those with impaired dexterity may find it difficult to hold the device steady for a relatively long period of time during medicament delivery. It may be beneficial to provide a device which is easier to handle during medicament delivery. However, simply reducing the biasing force produced by the control spring to the needle cover risks accidental actuation and needle safety issues. Therefore, it is desirable to provide a means to help a user of the device hold the device steady, by reducing the force needed to be applied by the user to overcome the biasing force. It is also desirable to reduce the user hold force, whilst minimising or removing any effect on the inserted needle depth, which can impact on the pharmacokinetic profile of the injected medicament and which does not require, or requires very minimal, casework modifications to the injection device. Advantageously, reducing the user hold force can also extend the usability of an injection device to longer injections, since it may be more comfortable for a user to hold the device at an injection site for a longer time. This may facilitate the delivery of medicaments comprising more viscous formulations.

FIG. 1 shows a schematic example of a cross section of a medicament delivery device 100 (hereinafter referred to as an injection device) according to one or more aspects of the present disclosure. The injection device 100 is configured to inject a medicament into a subject. The injection device 100 comprises an outer casing 102 (also referred to as a housing or injection device body) that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. A user typically removes cap 110 from the outer casing 102 before device 100 is operated.

As shown, casing 102 is substantially cylindrical and has a substantially constant diameter along the longitudinal axis of the device 100. The injection device 100 has a distal region 126 and a proximal region 128. The term "distal" refers to a location that is relatively closer to a site of injection, and the term "proximal" refers to a location that is relatively further away from the injection site.

The outer casing 102 is closed at a proximal end by a rear casing 114. A needle 116 and a retractable needle cover 118 (also referred to as a "needle sleeve" or "needle cover") extend from a distal end of the outer casing 102. The retractable needle cover 118 is biased axially in the distal direction of the injection device 100, for example using a control spring 120, which may also be referred to as a needle cover biasing member 120. The needle cover 118 is coupled to the outer casing 102 to permit axial movement of needle cover 118 relative to the outer casing 102. For example, the cover 118 can move in a longitudinal direction parallel to longitudinal axis 112. Specifically, movement of cover 118 in a proximal direction relative to the casing 102 can cause a needle 116 to extend from distal region of the casing 102, and outside a distal end of the cover 118.

The plunger 106 is biased towards the distal end of the injection device 100 by a biasing means, for example comprising a drive spring 122. The plunger 106 is retained in an initial position by a combination of the rear casing 114 and the collar 108, preventing the biasing means from displacing the plunger 106 in the distal direction. Activation of the injection device 100 causes the collar 108 to rotate, which releases the plunger 106. Once released, the biasing means causes the plunger 106 to move in the distal direction (i.e., towards the needle 116 end of the injection device 100). The plunger 106 contacts a stopper 113 in the reservoir 104, displacing the stopper 113 in the distal direction and causing medicament stored in the reservoir 104 to be expelled from the injection device 100 via the needle 116.

Activation of the injection device 100 can occur via several mechanisms. For example, the needle 116 may be fixedly located relative to the casing 102 and initially be located within an extended needle cover 118. Proximal movement of the needle cover 118 by placing a distal end of the cover 118 against an injection site of the subject and moving the casing 102 in a distal direction will uncover the distal end of the needle 116. Such relative movement allows the distal end of the needle 116 to extend into the injection site. Such insertion is termed "manual" insertion as the needle 116 is manually inserted via the user's manual movement of the casing 102 relative to cover 118. Retraction of the cover 118 into the casing 102 causes the collar 108 to rotate, releasing the plunger 106.

Another form of activation is "automated", whereby the needle 116 moves relative to casing 102. Such insertion can be triggered by movement of the cover 118 and/or by another form of activation, for example, a user actuation of a button (not shown) of the injection device 100.

Typically, the user presses the needle cover 118 against an injection site to push the needle cover 118 at least partially into the device casing 102. The exposed needle 116 is pushed into the injection site of the subject. In a holding position, medicament is automatically dispensed from the needle 116 via an automated mechanism. A user typically holds the needle cover 118 in the holding position for a predetermined period of time to ensure that a correct dose of medicament is dispensed from the device 100, before removing the device 100 from the injection site.

The spring biasing force 130 from the control spring 120 against which the user applies a force to move the needle cover 118 is one component of an "activation force" of the device 100. The activation force refers to the force or force profile that the user exerts on the device 100 to move the needle cover 118 from the extended position shown in FIG. 1 to a retracted position within the casing 102 for medicament delivery (see for example FIG. 4B). If this force or force profile is not well balanced, it can lead to difficulty in activating the device 100 for some users, or increase the pain or anxiety associated with using the device 100.

Following injection, the needle 116 can be retracted within the cover 118. Retraction can occur when the cover 118 moves distally under the biasing of the control spring 120, i.e. under the action of the biasing force 130, as a user removes the device 100 from the injection site of the subject. Once a distal end of the cover 118 has moved past a distal end of the needle 116 such that the needle 116 is covered, the cover 118 may be locked in its extended position to prevent any (substantial) proximal movement of the cover 118 relative to the casing 102 (i.e., preventing any movement of the cover 118 that would uncover the needle 116). The cover 118 may be locked by a needle cover non-return element (not shown), such as a catch.

FIGS. 2 and 3 show a medicament delivery system 300 comprising a medicament delivery device 100 and a hold assistance device 200. The hold assistance device 200 has a receiving volume 202 for receiving the medicament delivery device 100. The medicament delivery device 100 may be substantially similar or identical to the injection device 100 shown in FIG. 1 and described above, in which like reference numerals denote alike elements. In the example shown, the medicament delivery device 100 and the hold assistance device 200 are configured to fit together to form the medicament delivery system 300, such that the hold assistance device 200 is arranged to circumscribe at least a portion of the medicament delivery device 100. The hold assistance device 200 may be configured to be assembled together with the medicament delivery device 100 to be supplied to a user as the medicament delivery system 300, or the hold assistance device 200 and the medicament delivery device 100 may be supplied separately to a user and the user may then assemble the hold assistance device 200 and the medicament delivery device 100 together to form the medicament delivery system 300. It is also envisaged that the hold assistance device 200 may be retrofitted to a medicament delivery device 100, and that the hold assistance device 200 may be used with medicament delivery devices other than that in the example shown in FIG. 1 and described above. In any case, it is envisaged that the hold assistance device 200 may be removable from the medicament delivery device 100, such that the hold assistance device 200 may be reusable. The hold assistance device 200 may also be disposable. The function of the hold assistance device 200 is that it serves to assist the user in the use of the medicament delivery device 100, as outlined below.

Figure 4A:
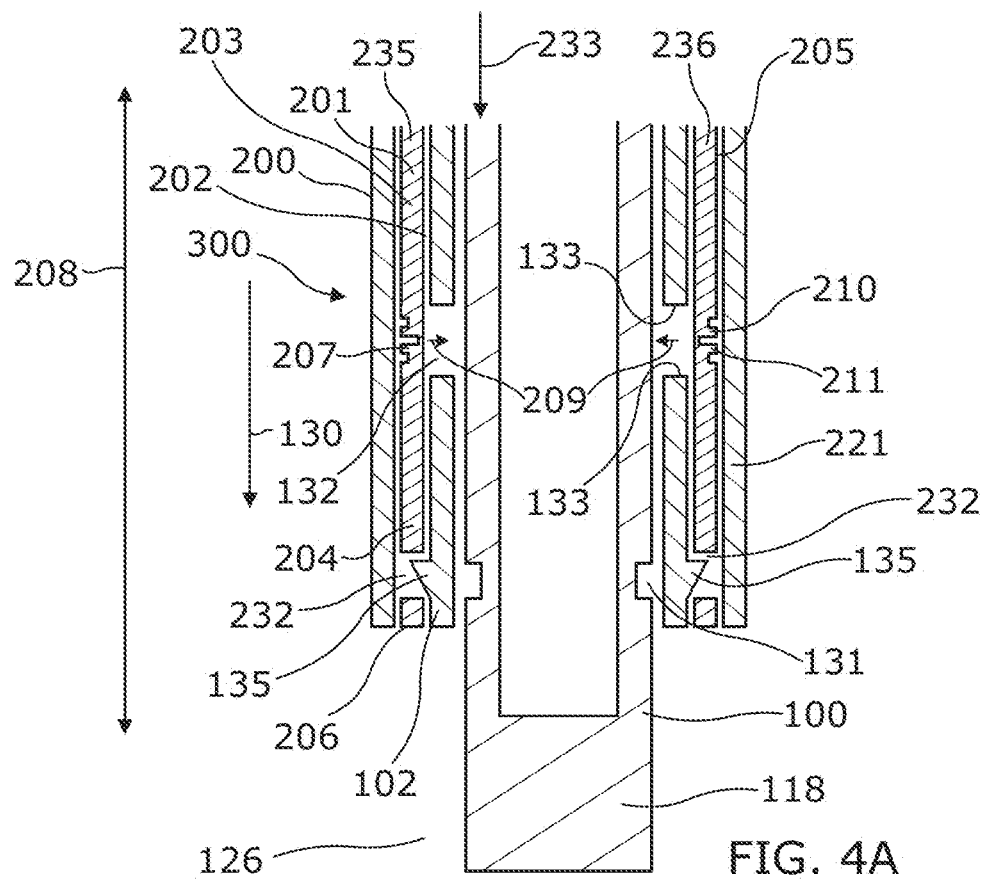
FIG. 4A shows a cross-sectional schematic view of a medicament delivery system.

FIG. 4A shows a cross-sectional schematic view of an exemplary hold assistance device 200 as attached to a medicament delivery device 100. For the sake of clarity and conciseness, only the main body 102 and the needle cover 118 of the medicament delivery device 100 are shown. The needle cover biasing member 120, for example a spring, is arranged to bias the needle cover 118 towards an extended position (see FIGS. 1 and 4A for example) in which the needle cover 118 protrudes form the main body 102 and a distal end 126 of the medicament delivery device 100 such that the needle 116 is covered by the needle cover 118. For example, when the needle cover 118 is in the extended position the needle cover biasing member 120, may for example be a compression spring in its natural extended, uncompressed state. Thus, when the needle cover 118 is in a retracted position (see FIG. 4C for example) in which the needle cover 118 is retracted in a proximal position relative to the extended position such that the needle cover 118 is retracted inside the main body 102 and the needle 116 is not covered by the needle cover 118, this goes against the biasing action of the needle cover biasing member 120. For example, where the needle cover biasing member 120 is a compression spring, this causes the needle cover biasing member 120 to be compressed.

Thus, a biasing force 130, for example a spring force 130, which acts in the direction shown in FIG. 4A for example by the arrow 130, inherently biases the needle cover 118 towards the extended position shown in FIGS. 1 and 4A. That is, because moving the needle cover 118 from the extended position to the retracted position goes against the action of the needle cover biasing member 120, for example by compressing a spring, the needle cover biasing member 120 hence biases the needle cover 118 axially in the distal direction 227 towards the extended position. Thus, once the needle cover 118 has been placed into the retracted position, in order to maintain the needle cover 118 in the retracted position so that the needle 116 remains uncovered and can be used for the required duration of time to deliver medicament to a patient, force is required by the user in order to counteract the biasing force 130, to prevent the needle cover 118 from extending outwards again.

The hold assistance device 200 acts to counteract the biasing force 130, by blocking axial movement of the needle cover 118 to provide an offsetting force 229 in order to counteract the action of the biasing force 130, thus resisting movement of the needle cover 118 from the retracted position back out to the extended position while a user is holding the medicament delivery device 100, for example at an injection site of a patient to deliver a medicament. In this manner, the hold assistance device 200 reduces the amount of force required from a user to hold the medicament delivery device 100 in a medicament delivery state in which the needle cover 118 is retracted, i.e. reduces the amount of force which needs to be applied by the user to resist the biasing force 130. The hold assistance device 200 does this by holding the needle cover 118 in place by blocking it from moving axially such that it is resisted from moving towards the distal end 126 or towards the proximal end 128. Thus, movement of the needle cover 118 from the retracted position along the axial direction towards the distal end 126 back into the extended position is prevented. That is, axial movement of the needle cover 118 is blocked, such that an offsetting force 229 is provided against the biasing force 130, in a direction that is generally opposite thereto. This holds the needle cover 118 in the retracted position, to prevent it from inadvertently moving towards the distal end 126 of the medicament delivery device 100, until medicament delivery is complete, at which point the needle cover 118 may be permitted to retract again under the action of the needle cover biasing member 120. In other words, the hold assistance device 200 provides a force 229 which can offset the user holding force of a standard two-step autoinjector. The force 229 is configured to act generally in a direction away from the distal end 126 and towards the proximal end 128, i.e. in a generally proximal direction.

Exemplary structures of the hold assistance device 200 which can provide for the resistance against the biasing force 130 shall now be described. FIGS. 4A to 4E show cross-sectional schematic views of an example of a hold assistance device 200 which provides such a resistive counterforce 229 against the biasing force 130 of the needle cover biasing member 120, to hold the needle cover 118 in place in the retracted position. In the example shown, the hold assistance device comprises a body 201 which comprises the receiving volume 202 for receiving the medicament delivery device 100. In the example shown, the body 201 is generally cylindrical and is arranged to circumscribe a medicament delivery device 100 received in the receiving volume 202. Although, it is envisaged that the body 201 may have any other suitable shape.

The hold assistance device 200 further comprises an outer housing 221 arranged to circumscribe the body 201, to provide an outer surface of the hold assistance device 200. In the example shown, the outer housing 221 is generally cylindrical and is in the form of a generally elongate sleeve, although it is envisaged that the outer housing 221 may have any other suitable form. Furthermore, it is envisaged that the outer housing 221 need not necessarily be present, and the outer housing 221 may serve for aesthetic or cosmetic purposes, to cover the body 201 such that the outer housing 221 is the outermost part of the hold assistance device 200 which is visible to a user of the device, and/or to provide protection to the body 201 to contribute to the ruggedness of the hold assistance device 200, and which may offer additional drop protection to the medicament delivery device 100. Therefore, whilst the following examples and accompanying illustrations describe and show an outer housing 221, it is to be understood that the outer housing 221 may be removed and need not be present. The outer housing 221 may be configured to be axially movable along the axial direction 208 relative to the medicament delivery device, for example relative to the main body 102 and/or the needle cover 118 thereof for example. The outer housing 221 may also be configured to be axially movable along the axial direction 208 relative to at least a portion of the body 201, as shall become evident from the following description of the body 201.

With further reference to FIG. 4A, the body 201 comprises a proximal portion 203 and a distal portion 204. The proximal portion 203 comprises a proximal end 205 of the body 201, and the distal portion 204 comprises a distal end 206 of the body 201. The proximal end 205 and the distal end 206 define an axial direction 208. That is, the axial direction 208 is oriented to extend linearly between the proximal end 205 and the distal end 206. Hereinafter, movement in the axial direction 208 away from the distal end 206 and towards the proximal end 205 may be referred to as movement in a proximal direction, and movement in the axial direction 208 away from the proximal end 205 and towards the distal end 206 may be referred to as movement in a distal direction. In the example shown, the body 201 is generally elongate and is arranged to extend between the proximal and distal ends 205, 206.

Arranged between the proximal portion 203 and the distal portion 204, the body 201 further comprises a connecting portion 207. That is, along the axial direction 208, the connecting portion 207 is arranged between the proximal and distal portions 203, 204. The connecting portion 207 is configured to flex into the receiving volume 202 in a flexing direction 209 that is radially inwards and is generally normal to the axial direction 208. Flexing of the connecting portion 207 into the receiving volume 202 causes the proximal portion 203 of the body 201 to move axially along the axial direction 208 relative to the distal portion 204. That is, the distal portion 204 of the body 201 is configured to remain relatively fixed, whilst the flexing of the connecting portion 207 causes the proximal portion 203 to move axially relative to the fixed distal portion 204, such that the proximal portion 203 is axially movable whilst the distal portion 204 is axially fixed. The connecting portion 207 may be relatively more flexible than the proximal and distal portions 203, 204 which may be relatively more rigid, to facilitate this flexing movement. For example, the connecting portion 207 may be manufactured from a relatively more flexible material than the proximal and distal portions 203, 204 which may be manufactured from a relatively more rigid material, and/or the geometry of the body 201 may be configured such that the connecting portion 207 is relatively flexible, for example by means of one or more cut-outs 226, 227, 228, and/or regions of decreased thickness, examples of which shall be described below.

Figures 8, 10:
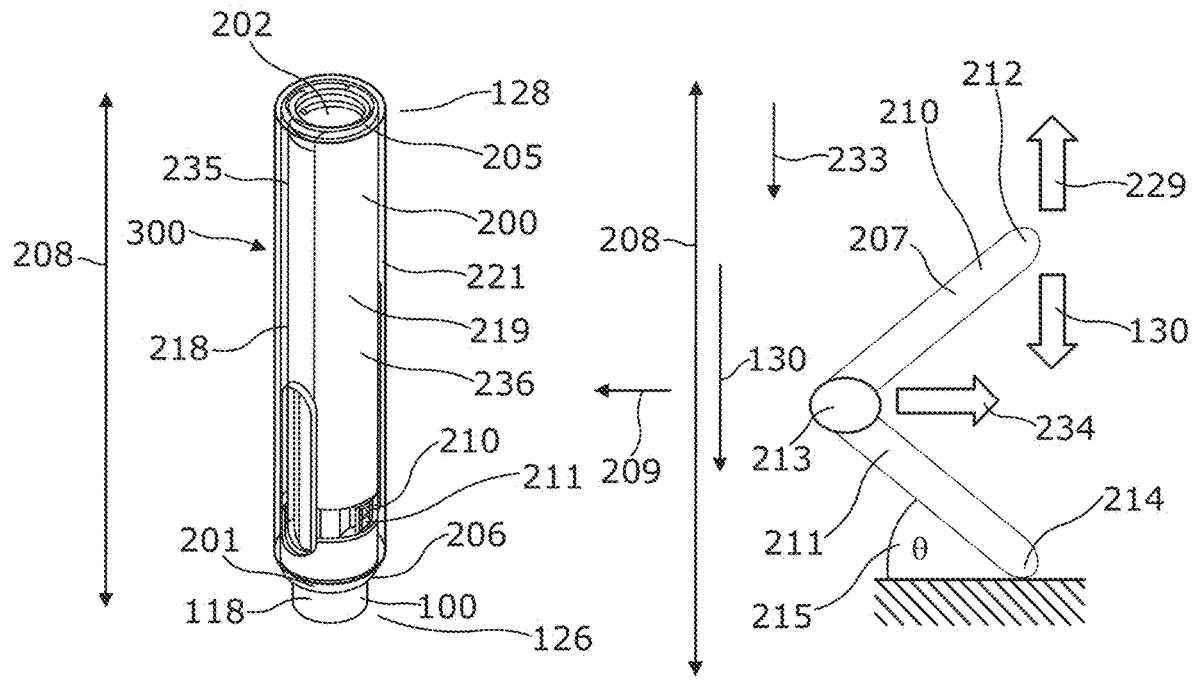
FIG. 8 shows a medicament delivery system.
FIG. 10 shows a connecting portion of a body of a hold assistance device.

In the examples shown herein and described above, the body 201 comprises two proximal portions 203, two distal portions 204, and two connecting portions 207, in the form of two halves or two sides of the body 201, for example in the form of a first clamshell portion 218 and a second clamshell portion 219 as shown in FIG. 8 and described below. For example, the body 201 may be generally cylindrical and may comprise a first elongate arm 235 and a second elongate arm 236. The first and second elongate arms 235, 236 may be arranged to be diametrically opposite to another, i.e. to be equally spaced apart from one another about a circumferential direction of the hold assistance device 200. The first and second elongate arms 235, 236 may be configured to be a mirror image of each other relative to the axial direction 208, in that they may be substantially identical to one another. Each of the first and second elongate arms 235, 236 comprises a respective proximal portion 203, a respective distal portion 204, and a respective connecting portion 207. The connecting portions 207 of the first and second elongate arms 235, 236 are each configured to flex radially inwards along the flexing direction 209, such that the arms 235, 236 are configured to flex towards each other. For the sake of clarity and conciseness, the following description shall refer to just one proximal portion 203, one distal portion 204, and one connecting portion 207, and hence to just one of the first and second elongate arms 235, 236. However, it is to be understood that since the first and second elongate arms 235, 236 are substantially identical and are both configured to flex in the flexing direction 209 substantially simultaneously with one another, said description shall also be applicable to the other one of the first and second elongate arms 235, 236.

It is also envisaged that the body 201 need not necessarily comprise two arms 235, 236 each comprising a respective proximal portion 203, a respective distal portion 204, and a respective connecting portion 207. Rather, the body 201 may comprise any number of one or more proximal portions 203, distal portions 204 and connecting portions 207. For example, the body 201 may comprise one or more arms 235, 236 each comprising a respective proximal portion 203, a respective distal portion 204, and a respective connecting portion 207. The one or more arms 235, 236 may be arranged to be equally or irregularly spaced apart from one another around a circumferential direction of the hold assistance device 200. It is also envisaged that the body 201 need not necessarily include one or more elongate arms 235, 236, and that the proximal, distal and connecting portions 203, 204, 207 may be in any other suitable form. For example, the body may be generally cylindrical or annular and may comprise a single proximal portion 203, a single distal portion 204, and a single connecting portion 207 each extending substantially the whole way around a circumferential direction of the hold assistance device 200. In the following description, examples shall be described which each have two elongate arms 235, 236 each comprising a respective proximal portion 203, distal portion 204 and connecting portion 207. However, it is to be understood that said description of the movement and functioning of the proximal, distal and connecting portions 203, 204, 207 is also applicable to other bodies having other forms or numbers of proximal, distal and connecting portions 203, 204, 207.

Figure 5A:
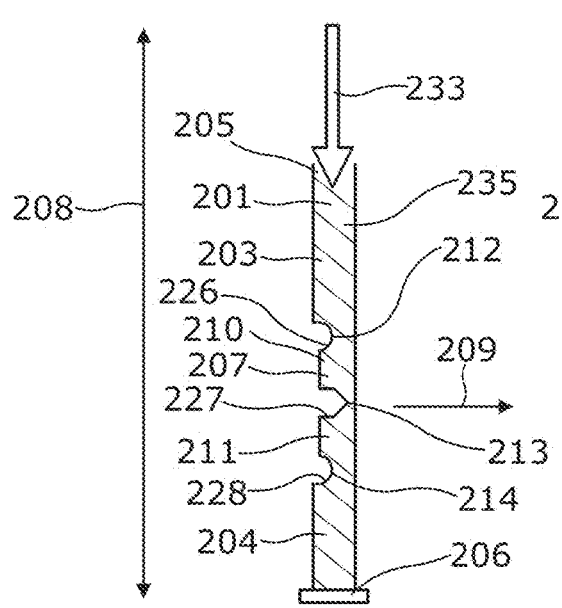
FIG. 5A shows a body of a hold assistance device.
Figure 5B:
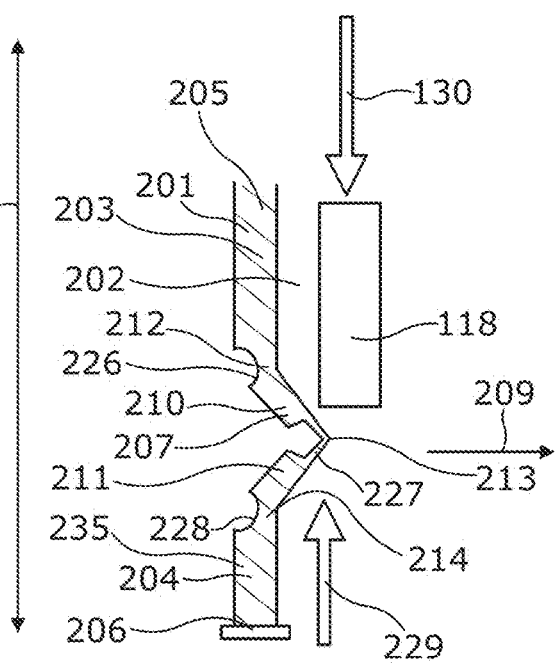
FIG. 5B shows a body of a hold assistance device and a needle cover of a medicament delivery device.

Referring now to FIGS. 5A and 5B, the body 201 is thus arrangeable in a first position (see FIG. 5A) in which the connecting portion 207 is in an unflexed state and the proximal portion 203 is spaced apart from the distal portion 204 along the axial direction 208 by a first distance, and a second position (see FIG. 5B) in which the connecting portion 207 is in a flexed state and the proximal portion 203 is spaced apart from the distal portion along the axial direction 208 by a second distance that is smaller than the first distance. In other words, because the distal portion 204 is configured to remain in an axially fixed position, with the proximal portion 203 being axially moveable thereto—i.e. such that the proximal end 205 is axially moveable along the axial direction 208 relative to the distal end 206-flexing of the connecting portion 207 brings the proximal portion 203 closer to the distal portion 204 and hence towards the distal end 206. As shown in FIG. 5B, the connecting portion 207 is configured to flex radially inwards along the flexing direction 209 to facilitate this axial movement of the proximal portion 203.

In the example shown in FIGS. 5A and 5B, the connecting portion 207 comprises a hinge, for example in the form of a two bar linkage. Although, it is also envisaged that other forms of connecting portion 207 may also be employed, for example other forms of hinge, or other forms of linkage. As shown in the example of FIG. 5A, the connecting portion 207 comprises a first connecting portion 210 and a second connecting portion 211. The first connecting portion 210 is arranged adjacent to the proximal portion 203, and the second connecting portion 211 is arranged adjacent to the distal portion 204. The first connecting portion 210 is hinged relative to the proximal portion 203 by a first pivot point 212. The first connecting portion 210 is hinged relative to the second connecting portion 211 by a second pivot point 213. The second connecting portion 211 is hinged relative to the distal portion 204 by a third pivot point 214. Thus, the connecting portion 207 may be described as being in the form of a two bar linkage, wherein each of the first and second connecting portions 210, 211 may be thought of as being a bar thereof, or may be described as being in the form of a three point hinge, in which the three pivot points 212, 213, 214 connect the proximal portion 203, the first connecting portion 210, the second connecting portion 211, and the distal portion 204. In the example shown, the first connecting portion 210 and the second connecting portion 211 are approximately equal in length. Though, it is envisaged that the first and second connecting portions 210, 211 may be any suitable length relative to one another—that is, they need not necessarily be approximately equal in length, and they may be of different lengths.

As shown in the examples of FIGS. 4A to 4E, FIGS. 5A and 5B and FIG. 7, the connecting portion 207 may comprise a first cut out 226, a second cut out 227 and a third cut out 228 in an outer surface of the body 201, to provide the first and second connecting portions 210, 211 and the three pivot points 212, 213, 214. The first cut out 226 is arranged between the proximal portion 203 and the first connecting portion 210. The second cut out 227 is arranged between the first and third cut outs 226, 228 and is arranged between the first and second connecting portions 210, 211. The third cut out 228 is arranged between the second connecting portion 211 and the distal portion 204. Each of the cut outs 226, 227, 228 results in the thickness of the body 201 being relatively thinner in the region of the cut outs 226, 227, 228, hence the material of the connecting portion 207 can be bent at each of the cut outs 226, 227, 228 to provide the aforementioned hinging. That is, the connecting portion 207 may be bent in the region of each of the cut outs 226, 227, 228, causing a pivoting movement, and hence providing for the three pivot points 212, 213, 214. For example, the connecting portion 207 may be bent in the region of the second cut out 227, thus causing the first connecting portion 210 to pivot relative to the second connecting portion 211, hence providing the second pivot point 213 between the first and second connecting portions 210, 211.

In the examples shown, the first and third cut outs 226, 228 are each generally semicircular, and the second cutout 227 is generally pentagonal (see FIG. 5A for example) or triangular (see FIG. 7 for example). Though, it is envisaged that each of the cut outs 226, 227, 228 may be any other suitable shape, and that the first and third cut outs 226, 228 need not necessarily be of the same shape to one another. For example, one or more of the first, second or third cut outs 226, 227, 228 may each comprise a semicircular, a triangular, a pentagonal, a square, a rectangle, a quadrilateral, a rhombus, a parallelogram, a diamond, a hexagonal, or any other suitable curved or linear sided shape. It is also envisaged that one or more of the first, second or third cut outs 226, 227, 228 may each comprise a slit or cut. It is also envisaged that the first and third cut outs 226, 228 need not necessarily be of approximately the same size to one another, and that the first, second and third cut outs 226, 227, 228 may be any suitable size to provide the desired flexing geometry.

Accordingly, the connecting portion 207 may be described as forming a knee joint or an elbow joint, because the connecting portion 207 can flex or bend inwards along the flexing direction 209 similarly to the movement of a knee joint or an elbow joint. Thus, upon application of a user applied downward force 233, for example by a user pressing the medicament delivery system 300 in a distal direction by placing it against the skin of a patient at an injection site to push the needle cover 118 inwards to retract inside the main body 201, said user applied downward force 233 causes the connecting portion 207 to flex such that body 201 is moved from the first position (see FIG. 5A) into the second position (see FIG. 5B). As shall be described below, the flexing of the connecting portion 207 to move the body 201 into the second position interacts with the medicament delivery device 100 and thus provides for an axial blocking action to prevent the needle cover 118 from being able to move axially, thus providing the offsetting force 229 against the biasing force 130 in order to hold the needle cover 118 in the retracted position for the required duration of time during medicament delivery.

Turning back to FIG. 4A, the distal portion 204 of the body 201 is configured to be coupled to the main body 102 of the medicament delivery device 100, such that the distal portion 204 is configured to remain fixed to the main body 102 along the axial direction 208. For example, the distal portion 204 may be configured to be mechanically coupled to the main body 102, such as by a clip or snap fit connection. In the example shown, the distal portion 204 comprises a receiving element 232 which may for example comprise an aperture, groove, recess or channel. The receiving element 232 is configured to receive a corresponding protruding element 135 of the main body 102 in order to couple the distal portion 204 to the main body 102. The protruding element 135 may be arranged to protrude in a generally radial direction that is generally normal to the axial direction 208, and may comprise a ramp or wedge shape having an inclined surface for example.

Since the proximal portion 203 is configured to be axially moveable relative to the distal portion 204 as a result of the flexing of the connecting portion 207, the proximal portion 203 is thus configured to be axially movable relative to the main body 102, to which the distal portion 204 is fixedly coupled. As shown in FIG. 4A, the main body 102 comprises a first receiving element 132, for example in the form of an aperture, configured to receive the connecting portion 207 when the connecting portion 207 is in a flexed state, i.e. when the body 201 is in the second position. That is, the connecting portion 207 is configured to flex into the first receiving element 132 in the flexing direction 209, such that the connecting portion 207 is configured to flex towards a central region of the receiving volume 202 via the first receiving element 132.

FIG. 4A shows the medicament delivery system 300 in an initial pre-use state before delivery of a medicament has taken place, which may also be referred to as a pre-activated state or a pre-activated position. In this state, the needle cover 118 is in the extended position covering the needle 116, and the body 201 is in the first position such that the connecting portion 207 is in an unflexed state. Once it is desired to prepare the medicament delivery device 100 for delivery of a medicament from the needle 116 to a patient, a user of the medicament delivery system 300 can then apply a user applied downward force 233 to the medicament delivery device 100, for example by pushing the distal end 126 against the skin of a patient at an injection site, thus causing the needle cover 118 to be pushed inwards to the retracted position.

Simultaneously, as the needle cover 118 moves from the extended position towards the retracted position (see FIGS. 4A, 4B and 4C sequentially for example), the application of the user applied downward force 233, pushing the medicament delivery device 100 against a surface such as the skin of a patient, simultaneously causes the proximal portion 203 of the connecting portion 207 of the body 201 to move distally towards the distal ends 206, 126. This may be thought of as the user pulling down the proximal portion 203 towards the distal portion 204, which remains relatively fixed. This distal axial movement of the proximal portion 203 causes the connecting portion 207 to flex inwards along the flexing direction 209 as described above, causing the body 201 to be placed into the second position, which may also be referred to as an activated position or an activated state.

Figure 4B:
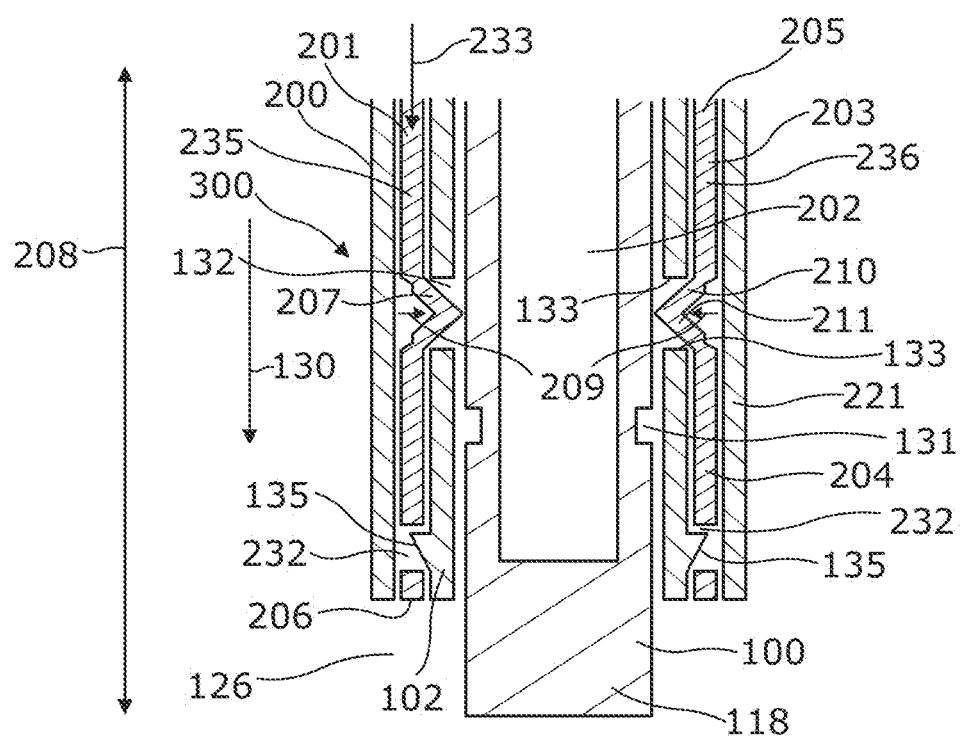
FIG. 4B shows a cross-sectional schematic view of a medicament delivery system.
Figure 4C:
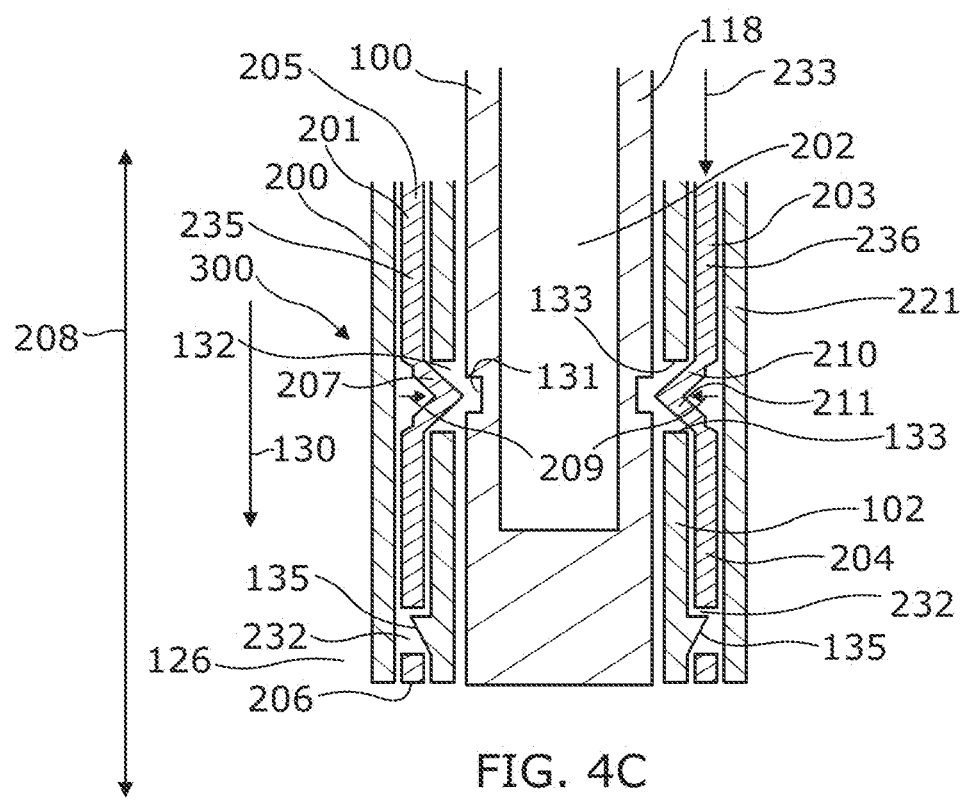
FIG. 4C shows a cross-sectional schematic view of a medicament delivery system.
Figure 4D:
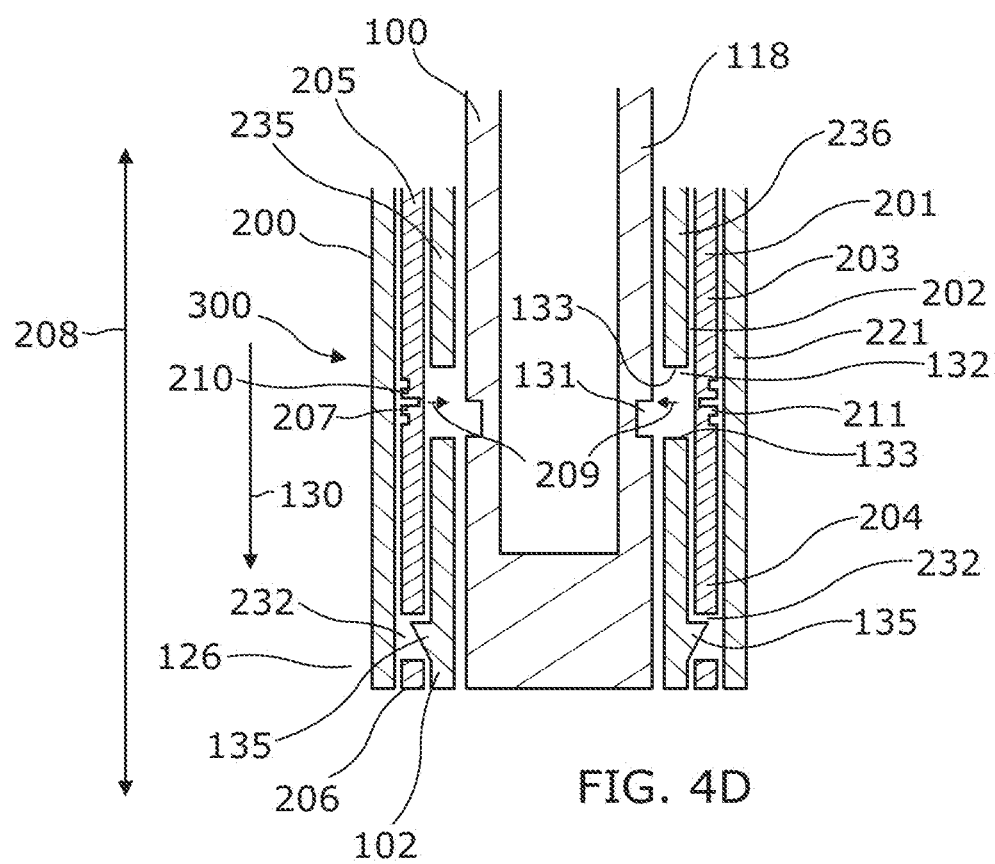
FIG. 4D shows a cross-sectional schematic view of a medicament delivery system.
Figure 4E:
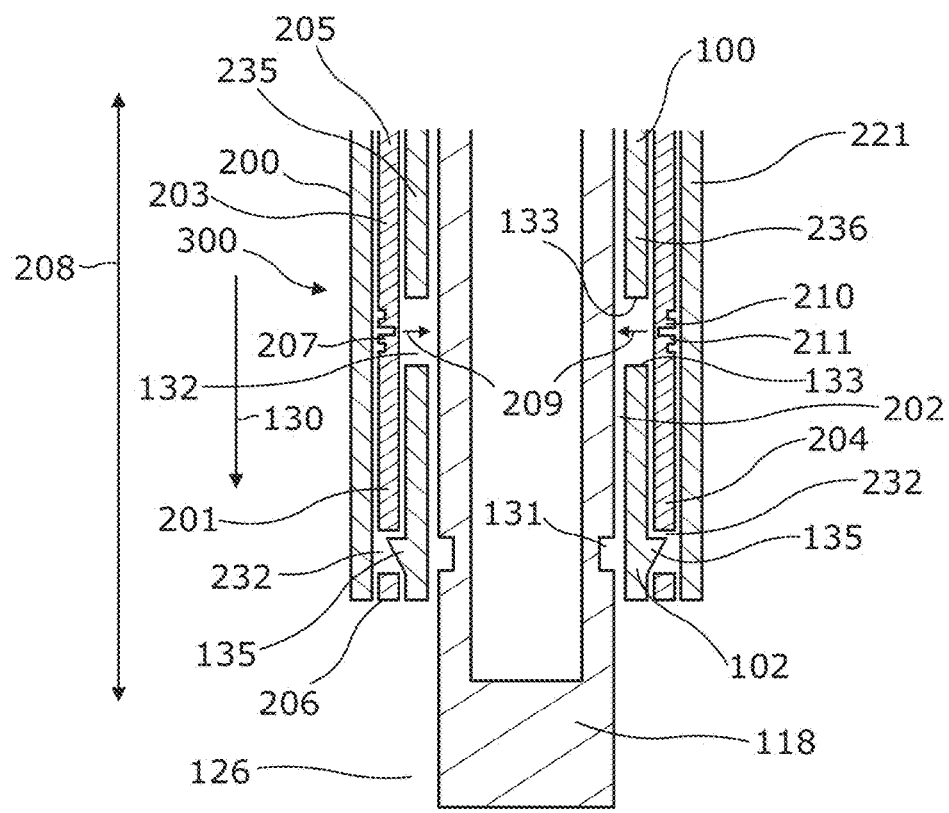
FIG. 4E shows a cross-sectional schematic view of a medicament delivery system.

In the example shown, along the axial direction 208, the first receiving element 132 is axially positioned relative to the connecting portion 207 of the body 201 such that distal downwards movement of the proximal portion 203 to place the connecting portion 207 into the flexed state causes the connecting portion 207 to become aligned with the first receiving element 132 such that when it is in its flexed state it protrudes into and is received by the first receiving element 132, as shown in FIG. 4B. FIG. 4B shows the needle cover 118 in an intermediate position between the extended position and the retracted position. That is, FIG. 4B shows the needle cover 118 during its proximal movement from the extended position to the retracted position, as the body 201 is placed into the second position. FIG. 4C shows the needle cover 118 at the end of its proximal movement from the extended position to the retracted position, i.e. once it has reached the retracted position. Thus, in FIG. 4C, the needle cover 118 is in the retracted position and the connecting portion 207 is flexed such that the body 201 is in the second position. The position shown in FIG. 4C may be referred to as a delivery position or a delivery state.

As described above, the connecting portion 207 is configured to flex into the receiving volume 202 and thus protrude thereinto, being received in the first receiving element 132 of the main body. Since the main body 102 is fixed axially along the axial direction, and the distal portion 204 of the body 201 is fixed to the main body 102, this means that when the connecting portion 207 is flexed such that the body is in the second position, the flexed connecting portion 207 is prevented from moving axially in either the proximal or distal direction, and is also prevented from unflexing. This is because surfaces 133 of the first receiving element 132 which are generally normal to the axial direction 208 bear against the flexed connecting portion 207 and thus prevent it from being able to move axially and/or pivotally relative to the axial direction 208. Hence, when the body 201 is in the second position and the connecting portion 207 is received in the first receiving element 132, the connecting portion 207 is axially locked in place. Hence, the proximal portion 203 is also axially locked in place. In other words, the first receiving element 132 locks the body 201 into the second position.

Furthermore, the needle cover 118 similarly comprises a second receiving element 131, which may be in the form of an aperture, a groove, a channel or a recess for example. The second receiving element 131 is also configured to receive the flexed connecting portion 207, such that when the body 201 is in the second position, the flexed connecting portion 207 is arranged to flex into the receiving volume 202 such that it extends radially inwards along the flexing direction 209, passing first through the first receiving element 132 in the main body 102, and then into the second receiving element 131 in the needle cover 118. The needle cover 118 is axially moveable along the axial direction 208 as described above, and the second receiving element 131 is positioned along the length of the needle cover 118 such that when the needle cover 118 is in the extended position (see FIG. 4A), or an intermediate position (see FIG. 4B for example), the second receiving element 131 is not aligned with the first receiving element 132 or the connecting portion 207 along the axial direction 208. That is, when the needle cover 118 is not in the retracted position, the second receiving element 131 is axially spaced apart from the first receiving element 132 and the connecting portion 207 along the axial direction 208. However, when the needle cover 118 is in the retracted position (see FIG. 4C for example), the second receiving element 131 is axially aligned with the first receiving element 132 and the flexed connecting portion 207 along the axial direction 208, shown in FIG. 4C for example. Thus, when the connecting portion 207 is in the flexed state wherein the body 201 is in the second position, and when the needle cover 118 is in the retracted position, the connecting portion 207 is flexed into the second receiving element 131 such that it is received thereby.

As described above, the distal portion 204 of the body 201 is fixedly coupled to the main body 102 such that it is not axially movable relative thereto, and when the connecting portion 207 is flexed it is axially constrained from axially moving or flexing by the first receiving element 132 of the main body 102, hence the body 201 is locked in place by the main body 102 when the connecting portion 207 is flexed. Since flexing the connecting portion 207 and placing the needle cover 118 into the retracted position causes the connecting portion 207 to flex into and be received by the second receiving element 131 of the needle cover 118, this causes the needle cover 118 to also be locked in place along the axial direction such that it is prevented, or at least resisted, from moving along the axial direction 208. That is, the connecting portion 207 is configured to protrude into and bear against the second receiving element 131, such that the physical position of the connecting portion 207, which itself is axially locked in place relative to the main body 102 as described above, acts to block the needle cover 118 from axially moving. Thus, whilst the needle cover biasing member 120 acts to bias the needle cover 118 axially in the distal direction away from the retracted position and towards the extended position, applying a biasing force 130, the needle cover 118 is nevertheless prevented from moving from the retracted position towards the extended position by the blocking action of the flexed connecting portion 207.

In the position shown in FIG. 4C, the medicament delivery device 100 may be ready for delivery of a medicament via the needle 116 to an injection site of a patient to commence. The needle cover 118 is held in place in the retracted position, providing an offsetting force 229 against the action of the biasing force 130, and hence reducing the magnitude of a user hold force required to hold the medicament delivery device 100 in this state and overcome the biasing force 130 to keep the needle cover 118 in the retracted position for safe and accurate medicament delivery via the needle 116. This blocking action can be used to selectively lock the needle cover 118 in place, to help retain the needle cover 118 in the retracted position for the required duration of time, and prevent it from inadvertently moving distally into the extended position.

The medicament delivery system 300 may be kept in the position shown in FIG. 4C for as long as is needed for a user of the medicament delivery system 300 to deliver medicament from the needle 116 of the medicament delivery device 100 to an injection site of a patient, in order to reduce the amount of force needed to be applied by the user to retain the needle cover 118 in the retracted position in which the needle 116 is uncovered and can be used to deliver medicament. After delivery of the medicament from the needle 116 has been completed, the medicament delivery device 100 may be removed from the injection site of the patient, thus the hold force is no longer required. At this point, it may be desirable to recover the needle 116 with the needle cover 118 for safety and hygiene reasons, to help ensure safe removal and disposal of the medicament delivery device 100 from the injection site. Thus, it may be desired to bring the needle cover 118 back into the extended position in which it covers the needle 116. In order to allow the needle cover 118 to revert back into its extended position, under the action of the biasing force 130, the offsetting force 229 can be removed, or at least reduced in magnitude, such that the action of the needle cover biasing member 130 may be permitted to cause the needle cover 118 to move back into its extended position. This can be done by unflexing the connecting portion 207, such that it no longer blocks axial movement of the needle cover 118.

In order to unflex the connecting portion 207, the user applied downward force 233 can be removed, or at least reduced in magnitude, for example by moving the medicament delivery system 300 away from a surface such as the skin of a patient at an injection site, such that said surface no longer provides a reaction force against the medicament delivery system 300. By removal of the user applied downward force 233, the flexible connecting portion 207 may thus be caused to unflex, allowing the proximal portion 203 to move axially in the proximal direction, the connecting portion 207 unflexing radially outwards in a direction generally opposite to the flexing direction 209, into the position shown in FIG. 4D. In the position shown in FIG. 4D, the body 201 is in the first position wherein the connecting portion 207 is in an unflexed state.

Then, because the connecting portion 207 is no longer flexed such that it no longer protrudes into and is no longer received by the first receiving element 132 of the main body 102, this causes the needle cover 118 to be unlocked from the retracted position such that it is no longer blocked from moving axially. Firstly, this is because when the connecting portion 207 is unflexed it also no longer protrudes into and is no longer received by the second receiving element 131 of the needle cover, hence it no longer blocks axial movement of the needle cover 118 and bears against it to hold it in place. Second, this is because since unflexing the connecting portion 207 causes it to no longer be received by the first receiving element 132 of the main body 102, the body 201 is no longer axially fixed in place, so the proximal portion 203 is free to move axially in the proximal direction. Thus, the connecting portion 207 can unfold or unflex, the proximal portion 203 can slide back upwards in the proximal direction, and the body 201 is thus moved back into the first position. As such, the needle cover 118 is thus no longer axially constrained and is free to move axially in the distal direction to move back into the extended position under the action of the biasing force 130 of the needle cover biasing member 120, to the position shown in FIG. 4E. In the position shown in FIG. 4E, the body 201 is in the first position and the needle cover 118 is extended, as in FIG. 4A.

In the examples described above, the main body 102 comprises a first receiving element 132 and the needle cover 118 comprises a second receiving element 131, the first and second receiving elements 132, 131 arranged to received the flexed connecting portion 207, and thus being positioned along the axial direction 208 relative thereto appropriately. However, it is also envisaged that the first and second receiving elements 132, 131 need not necessarily be present. For example, the geometry of the hold assistance device 200 relative to the medicament delivery device 100 may be designed such that the flexed connecting portion 207 need not necessarily be axially alignable with a first and/or second receiving element 132, 131 in order to provide a blocking function to resist axial movement of the needle cover 118. For example, the connecting portion 207 may be configured to directly interface with an exposed distal end portion of the needle cover 118 towards or at the distal end 126 of the medicament delivery device 100, without having to first pass through a first receiving element 132 in the main body 102. Also, the connecting portion 207 may be configured to directly interface with the outer surface of an exposed distal end portion of the needle cover 118 towards or at the distal end 126 of the medicament delivery device 100, without the need for a second receiving element 131 such as a recess, channel, aperture or groove for example. Rather, the connecting portion 207 may be configured to protrude towards and to abut a plain outer cylindrical surface of a needle cover 118, to apply a clamping force thereto along the flexing direction 209, to frictionally resist or impede its axial movement. In such an example, modifications to the main body 102 and/or to the needle cover 118 may be avoided, for example by avoiding the need to provide the first receiving element 132 and/or the second receiving element 131, thus providing that the hold assistance device 200 may be implemented as an external add-on which can be retrofitted to a pre-existing medicament delivery device 100 without the need for modifications thereto.

The hold assistance device 200 may further comprise a body biasing member 230 (see FIG. 6 for example) to bias the body 201 in the proximal direction, i.e. towards the proximal end 128 of the medicament delivery device 100. That is, the body biasing member 230 may be arranged to bias the body 201 towards the first position in which the proximal portion 203 is arranged to be axially further apart from the distal portion 204 than when the body 201 is in the second position such that the connecting portion 207 is flexed. Thus, the body biasing member 230 may be arranged to bias the body 201 away from the second position, such that the user applied downward force 233 is applied to exceed the magnitude of a body biasing member biasing force 231 (see FIG. 6 for example), to cause and allow the body 201 to move from the first position to the second position. Upon removal of or at least reduction of the magnitude of the user applied downward force 233, the body 201 is caused to move from the second position back to the first position, under the action of the body biasing member biasing force 231, which pulls it back up again in the proximal direction into the first position.

The body biasing member 230 may comprise a spring, such as an extension spring coupled to the proximal end 205 of the body 201 for example. For example, when the body 201 is in the first position, the extension spring may be in a natural, unstretched state, and when the body 201 is in the second position, the extension spring may be in an extended, stretched state, such that the extension spring naturally wants to go back to its natural, unstretched state, thus biasing the proximal end 205 of the body 201 in the proximal direction towards the first position. It is also envisaged that the body biasing member 230 may comprise any other suitable type of spring, or any other suitable type of biasing member. In the example shown in FIG. 6, the body biasing member 230 is arranged to bias the body 201 towards the first position, i.e. in the proximal direction, relative to the outer housing 221.

FIG. 7 shows another example of a medicament delivery system 300, wherein like reference numerals denote like elements. In the example shown, the hold assistance device 100 is generally similar to those described above and shown in FIGS. 2 to 4E, except that instead of the first receiving element 132 of the main body 102 comprising surfaces 133 arranged generally normal to the axial direction 208, the first receiving element 132 instead comprises inclined surfaces 134 which are angled relative to the axial direction 208 and are hence also angled relative to the normal thereto. In the example shown, the surfaces 133 are angled away from one another such that the first receiving element 132 is relatively narrower proximate to the needle cover 118 and is relatively wider proximate to the outside of the medicament delivery device 100 and hence proximate to the body 201. In this manner, the first receiving element 132 may be sized and shaped to correspond with the angles of the first and second connecting portions 210, 211 when the connecting portion 207 is flexed.

With further reference to FIG. 7, FIG. 7 shows an enlarged sectional view which illustrates that the connecting portion 207 may further comprise a protruding portion 216, for example which comprises a ramp shape 217. The protruding portion 216 is arranged to protrude radially inwards along the flexing direction 209 and is configured to be received in the second receiving element 131 of the needle cover 118. The protruding portion 216 may be shaped to facilitate the receiving of the connecting portion 207 in the second receiving element 131. In the example shown, the protruding portion 216 is arranged approximately at the centre of the connecting portion 207 along the axial direction 208. Though, it is envisaged that the protruding portion 216 need not necessarily be arranged approximately at the centre of the connecting portion 207 and that it may be positioned at any other suitable location along the axial direction 208, for example not at a location that is equidistant from the first and third pivot points 212, 214. Advantageously, the protruding portion 216 may provide for greater control over the offsetting force 229 and hence for greater control of the user applied downward force 233, and may allow for greater design flexibility. Providing a ramp shape 217 on the connecting portion 207 may allow a horizontal force component to be adjusted independently of the angle θ 215, to provide for greater regulation of a gearing ratio between the offsetting force 229 and the biasing force 130. The protruding portion 216 may also be present in the other examples described and shown herein, for example in the examples shown in FIGS. 4A to 4E.

With reference to FIG. 8, the body 201 may be generally in the form of a clamshell configured to close around the medicament delivery device 100 to couple the hold assistance device 200 thereto. The outer housing 221 may then for example be configured to slidably receive the body 201 and the medicament delivery device 100 to circumscribe them. The body 201 may comprise a first clamshell portion 218 and a second clamshell portion 219, which may each for example comprise approximately half of the body 201 in a circumferential direction that is generally normal to the axial direction 208, as shown in FIG. 9 for example. The first and second clamshell portions 218, 219 may be hingeably connected to one another, or hingeably integrally formed together, such that the body 201 can be closed around the medicament delivery device 100, and such that conversely the body 210 can be opened to remove the hold assistance device 200 from the medicament delivery device 100. As shown in FIG. 9, the body 201 may further comprise an interlock mechanism 220 configured to couple the first and second clamshell portions 218, 219 together once closed around the medicament delivery device 100, and optionally also to couple the distal portion 204 to the main body 102 of the medicament delivery device 100. The interlock mechanism 220 may for example comprise a clip, a pin, and/or a snap fit or the like.

Turning now to FIG. 10, the hold assistance device 200 may be configured such that the magnitude of the offsetting force 229 is scaled as required, to be designed to be several times stronger than the biasing force 130 of the needle cover biasing member 120, to ensure that substantially all of the biasing force 130 is offset, to sufficiently aid the user in the operation of the medicament delivery system 300 by reducing the hold force required during injection. For example, the magnitude of the offsetting force 229 may be scaled as required based the value of an angle $\theta$ 215 which is the angle between the first and second connecting portions 210, 211 and the flexing direction 209, when the connecting portion 207 is flexed to its maximum allowed flexing extent, i.e. the angle by which when the connecting portion 207 is flexed as far as possible into the first receiving element 132, the first and second connecting portions 210, 211 are angled relative to the normal to the axial direction 208. In some examples, the biasing force 130 generated by the needle cover biasing member 120 may be between approximately 10 N and 15 N, and the magnitude of the offsetting force 229 may be scaled accordingly to offset the biasing force 130, for example to be greater than the biasing force 130, or for example to be approximately at least two, three, four, five or six times greater than the biasing force 130.

Figure 11:
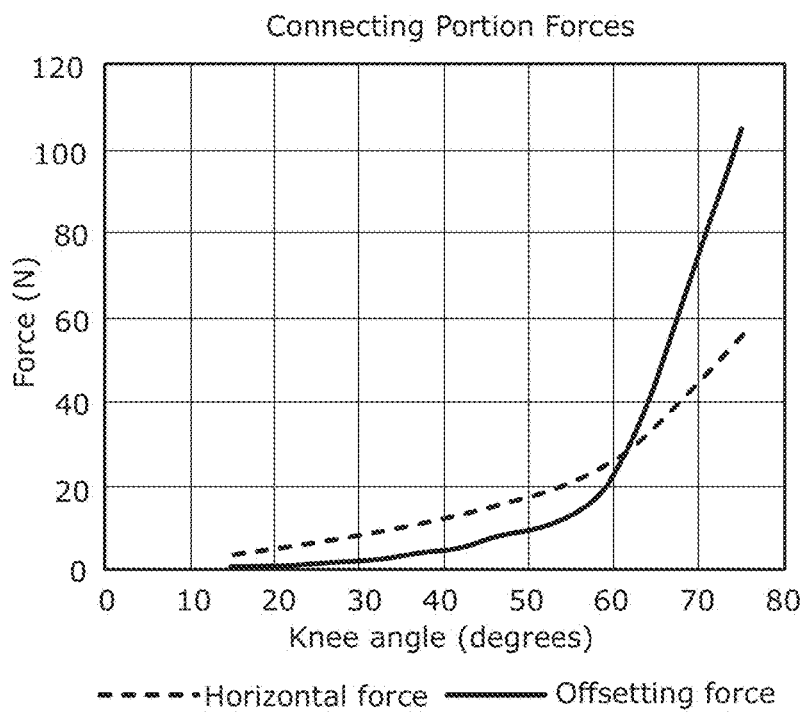
FIG. 11 shows a graph of force plotted against knee angle.

FIG. 11 shows a graph of force (in Newtons, N) plotted against knee angle, the angle $\theta$ 215 (in degrees, °). Two forces are plotted: the horizontal force 234 acting at the second pivot point 213 on the flexed connecting portion 207, and the offsetting force 229 exerted by the flexed connecting portion 207. When the bend in the flexed connecting portion 207 is relatively shallow, i.e. such that the angle $\theta$ 215 (See FIG. 10) is relatively larger, the flexed connecting portion 207 can exert a relatively larger magnitude of offsetting force 229, thus providing a greater mechanical advantage to the user, and hence reducing the magnitude of the user hold force 233 required to hold the needle cover 118 in the retracted position. Conversely, when the bend in the flexed connecting portion 207 is relatively deeper, i.e. such that the angle $\theta$ 215 (See FIG. 10) is relatively smaller, the flexed portion 207 may exert a relatively diminished upward force as the offsetting force 229, and hence the user may be required to exert a larger hold force 233 required to hold the needle cover 118 in the retracted position.

Thus, shallower bends and hence larger values of the angle $\theta$ 215 can advantageously result in a larger offsetting force 229, such that the amount of force required to be applied by the user is reduced, to provide increased hold assistance to the user during medicament delivery, as it will require less physical effort for them to hold the medicament delivery device 100 in place with the needle cover 118 in the retracted position. This is evident from FIG. 11, which shows that both the horizontal force 234 and the offsetting force 229 increase as the value of the angle $\theta$ 215 increases, i.e. as the bend of the flexed connecting portion 207 becomes shallower, i.e. closer to the straight unflexed position wherein the body 201 is in the first position. The first receiving element 132 and/or the second receiving element 131 may be sized and shaped, for example by choosing a particular axial separation between the surfaces 133 or 134, to control by how much the connecting portion 207 is permitted to flex, for example to limit it from flexing too deeply beyond a certain value of the angle $\theta$ 215. The angle $\theta$ 215 may be for example between approximately 15° and 75°, preferably between approximately 45° and 75°, more preferably between approximately 60° and 75°, and even more preferably between approximately 70° and 75°, in order to help maximise the mechanical advantage to reduce the effort required by the user.

Figure 12:
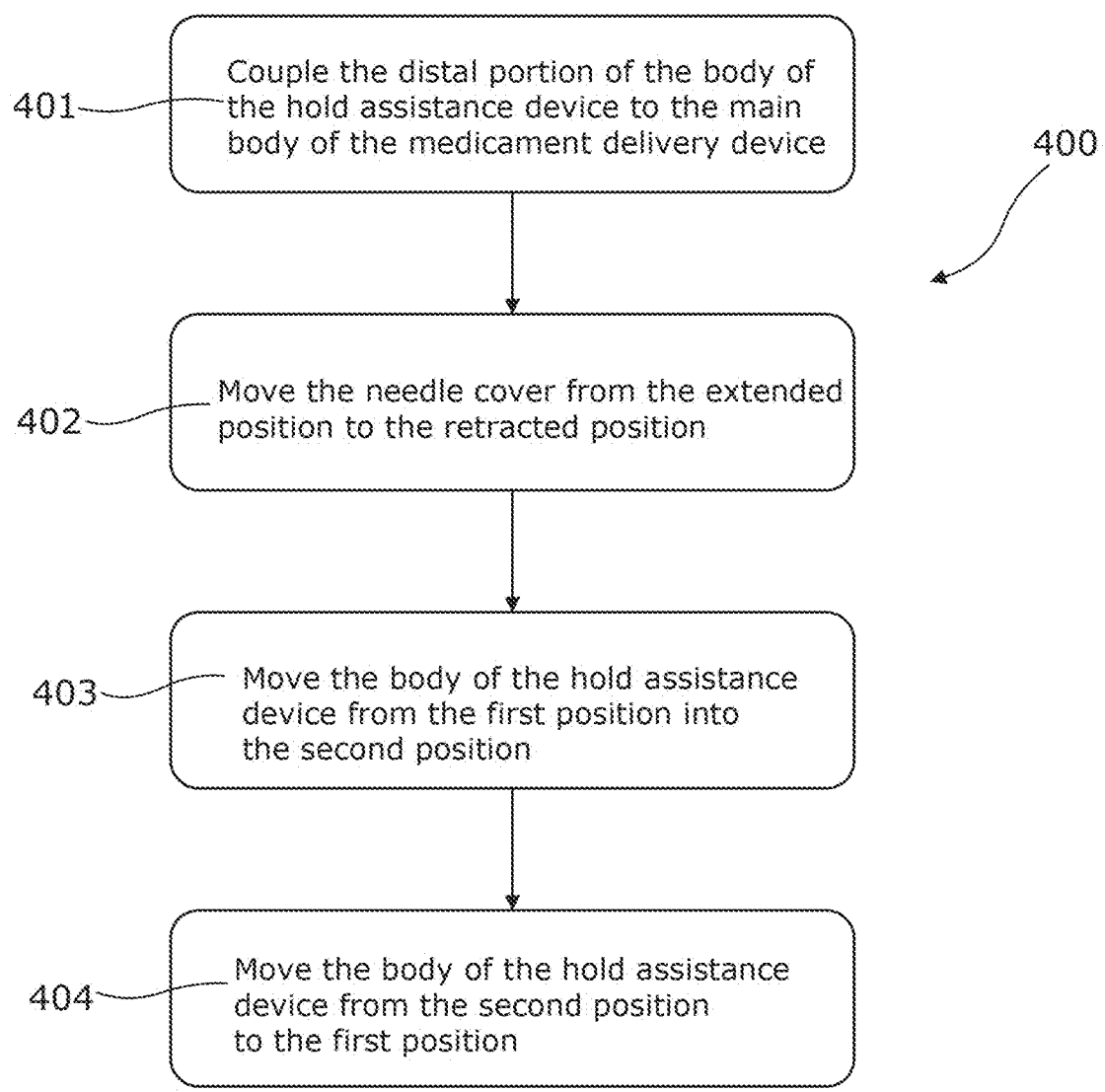
FIG. 12 shows a flowchart illustrating a method of operating a medicament delivery system.

FIG. 12 shows a flowchart depicting an exemplary method 400 of operating a medicament delivery system 300, for example medicament delivery systems 300 as described above. The exemplary method of FIG. 12 comprises a step 401 of coupling the distal portion 204 of the body 201 of the hold assistance device 200 to the main body 102 of the medicament delivery device 100, in order to couple the hold assistance device 200 to the medicament delivery device 100. Step 402 comprises moving the needle cover 118 from the extended position to the retracted position, for example by placing the medicament delivery device 100 against a surface such as the skin of a patient at an injection site, and applying a user applied downward force 223 in the distal direction in a direction towards the surface, thus pushing the needle cover 118 against said surface and causing it to be pushed inside the main body 102 to retract thereinside.

Step 403 comprises moving the body 201 of the hold assistance device 100 from the first position in which the connecting portion 207 is in an unflexed state into the second position in which the connecting portion 207 is in a flexed state and is arranged to protrude into the receiving volume 202, such that the connecting portion 207 is arranged to resist axial movement of the needle cover 118 from the retracted position to the extended position. Step 403 may occur after step 402, or step 403 may occur simultaneously with step 402. In either case, it may be the occurrence of step 402 that may cause step 403 to happen. For example, moving the needle cover 118 from the extended position to the retracted position may cause the body 201 of the hold assistance device 200 to be automatically moved from the first position into the second position. As another example, after or during moving the needle cover 118 from the extended position to the retracted position, a user of the medicament delivery system 300 may manually move the body 201 into the second position, for example by gripping the body and sliding or pushing it downwards relative to the main body 102 in the distal direction. For example, a user pushing the medicament delivery device 100 against a surface such as an injection site of a patient to move the needle cover 118 from the extended position to the retracted position may cause the user to simultaneously apply a pushing force to the body 201 to cause the proximal portion 203 to move distally to cause the connecting portion 207 to flex and the body 201 to be placed in the second position.

Step 404 comprises moving the body 201 of the hold assistance device 200 from the second position to the first position to cause the connecting portion 207 to unflex such that it no longer protrudes into the receiving volume 202 and the needle cover 118 is free to move axially in the distal direction towards the extended position under the biasing force 130 of the needle cover biasing member 120. In the method 400, between step 403 of moving the body 201 of the hold assistance device 200 from the first position to the second position and step 404 of moving the body 201 of the hold assistance device 200 from the second position to the first position, a user of the medicament delivery system 300 may hold the medicament delivery device 100 for a required duration of time at an injection site of a patient. For example, the user may hold the medicament delivery device 100 at the injection site for the amount of time required for completion of delivery of a medicament from the needle 116 to be complete.

Once the body 201 has been moved back into the first position, the method 400 may further comprise a step (not shown) of moving the needle cover 118 from the retracted position back into the extended position, such that the needle 116 is covered, which may be desirable for reasons of safety and hygiene. The needle cover 118 may be moved from the retracted position back into the extended position by, for example, removing a user applied downward force 233 acting on the medicament delivery device 100, for example by moving the medicament delivery device 100 away from an injection site of a patient. For example, by moving the medicament delivery device 100 in the proximal direction away from the skin of a patient, this may remove the user hold force 233 pushing the needle cover 118 inside the housing 102 as a result of pressing the needle cover 118 against the skin, such that when the medicament delivery device 100 is moved away, the needle cover 118 is permitted to extend outwards again under the action of the biasing force 130 of the needle cover biasing member 120, which is no longer offset by the offsetting force 229 since axial movement of the needle cover 118 is no longer blocked by the connecting portion 207, which is no longer flexed.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')$_2$ fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1: 2014 (E). As described in ISO 11608-1: 2014 (E), needle-based injection systems may be broadly distinguished into multi-dose container systems and single-dose (with partial or full evacuation) container systems. The container may be a replaceable container or an integrated non-replaceable container.

As further described in ISO 11608-1: 2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS 100-injection device
102-outer casing/housing/main body
104-reservoir
106-plunger
108-collar
110-cap
112-longitudinal axis
113-stopper
114-rear casing
116-needle
118-needle shroud/sleeve/cover
120-control spring/needle cover biasing member
122-drive spring
124-injection site
126-distal end
128-proximal end
130-biasing force
131-second receiving element
132-first receiving element
133-first receiving element normal surfaces
134-first receiving element inclined surfaces
135-main body protruding element
200-hold assistance device
201-body
202-receiving volume
203-proximal portion
204-distal portion
205-proximal end
206-distal end
207-connecting portion
208-axial direction
209-flexing direction
210-first connecting portion
211-second connecting portion
212-first pivot point
213-second pivot point
214-third pivot point
215-angle θ
216-protruding portion
217-ramp
218-first clamshell portion
219-second clamshell portion
220-interlock
221-outer housing
226-first cut out
227-second cut out
228-third cut out
229-offsetting force
230-body biasing member
231-body biasing member biasing force
232-receiving element
233-user applied downward force
234-horizontal force
235-first elongate arm
236-second elongate arm
300-medicament delivery system
400-method
401-method step
402-method step
403-method step

The invention claimed is:

1. A hold assistance device for use with a medicament delivery device, the hold assistance device comprising a body comprising:
a receiving volume for receiving a medicament delivery device;
a proximal portion comprising a proximal end of the body;
a distal portion comprising a distal end of the body, the proximal end and the distal end defining an axial direction; and
a connecting portion arranged between the proximal portion and the distal portion, wherein the connecting portion is configured to flex into the receiving volume in a direction generally normal to the axial direction, causing the proximal portion to move axially relative to the distal portion, and wherein the connecting portion comprises a hinge.

2. The hold assistance device of claim 1, wherein the body is arrangeable in:
a first position in which the connecting portion is in an unflexed state and the proximal portion is spaced apart from the distal portion along the axial direction by a first distance; and
a second position in which the connecting portion is in a flexed state and the proximal portion is spaced apart from the distal portion along the axial direction by a second distance that is smaller than the first distance.

3. The hold assistance device of claim 2, wherein the hold assistance device further comprises a body biasing member configured to bias the body towards the first position.

4. The hold assistance device of claim 1, wherein the connecting portion comprises a linkage.

5. The hold assistance device of claim 1, wherein the connecting portion comprises a first connecting portion arranged adjacent to the proximal portion, and a second connecting portion arranged adjacent to the distal portion, wherein the first connecting portion is hinged relative to the proximal portion by a first pivot point, the first connecting portion is hinged relative to the second connecting portion by a second pivot point, and the second connecting portion is hinged relative to the distal portion by a third pivot point.

6. The hold assistance device of claim 5, wherein the first connecting portion and the second connecting portion are approximately equal in length along the axial direction.

7. The hold assistance device of claim 5, wherein the connecting portion is configured to flex into the receiving volume in a radial direction generally normal to the axial direction, such that when the connecting portion is in a flexed state, the first connecting portion and the second connecting portion are configured to be angled relative to the radial direction by an angle of between approximately 15° and 75°.

8. The hold assistance device of claim 1, wherein the connecting portion comprises a protruding portion arranged to protrude towards the receiving volume in a direction generally normal to the axial direction.

9. The hold assistance device of claim 8, wherein the protruding portion is arranged approximately at the center of the connecting portion along the axial direction.

10. The hold assistance device of claim 8, wherein the protruding portion comprises a ramp comprising a surface that is inclined relative to the axial direction.

11. The hold assistance device of claim 1, wherein the distal portion is configured to be coupled to a main body of a medicament delivery device and to remain fixed relative thereto, and wherein the proximal portion is configured to be movable relative to the main body of the medicament delivery device along the axial direction.

12. The hold assistance device of claim 1, wherein the body is generally cylindrical and is configured to circumscribe a medicament delivery device.

13. The hold assistance device of claim 1, wherein the body comprises a clamshell portion configured to receive and close around a medicament delivery device.

14. The hold assistance device of claim 1, wherein the hold assistance device further comprises a housing arranged to circumscribe at least a portion of the body, wherein the proximal portion is configured to be movable relative to the housing along the axial direction.

15. A medicament delivery system comprising a hold assistance device and a medicament delivery device,
wherein the hold assistance device comprises a body comprising:
a receiving volume for receiving the medicament delivery device;
a proximal portion comprising a proximal end of the body;
a distal portion comprising a distal end of the body, the proximal end and the distal end defining an axial direction; and
a connecting portion arranged between the proximal portion and the distal portion, wherein the connecting portion is configured to flex into the receiving volume in a direction generally normal to the axial direction, causing the proximal portion to move axially relative to the distal portion,
wherein the medicament delivery device comprises:
a main body configured to receive a medicament cartridge and comprising a proximal end and a distal end;
a needle for delivery of medicament from the medicament cartridge;
a needle cover axially movable relative to the main body between:
an extended position in which the needle cover extends from the distal end of the main body and covers a distal end of the needle which protrudes from the main body; and a retracted position in which the needle cover is arranged in a proximal position relative to the extended position such that the distal end of the needle protrudes from a distal end of the needle cover; and
a needle cover biasing member configured to bias the needle cover axially in a distal direction towards the extended position,
wherein the distal portion of the body of the hold assistance device is configured to be coupled to the main body of the medicament delivery device, and the proximal portion of the body of the hold assistance device is configured to be movable relative to the main body of the medicament delivery device along the axial direction, and
wherein when the hold assistance device is coupled to the medicament delivery device and the connecting portion is in a flexed state, the connecting portion is arranged to resist axial movement of the needle cover.

16. The medicament delivery system of claim 15, wherein the main body comprises a first receiving element for receiving the connecting portion when the connecting portion is in the flexed state, such that when the hold assistance device is coupled to the medicament delivery device and the connecting portion is arranged in the flexed state, the connecting portion is configured to flex into the first receiving element to limit movement of the proximal portion of the body of the hold assistance device in the axial direction.

17. The medicament delivery system of claim 15, wherein the needle cover comprises a second receiving element for receiving the connecting portion when the connecting portion is in the flexed state and the needle cover is in the retracted position, such that when the hold assistance device is coupled to the medicament delivery device and the needle cover is in the retracted position and the connecting portion is arranged in the flexed state, the connecting portion is configured to flex into the second receiving element to resist movement of the needle cover axially in the distal direction towards the extended position.

18. The medicament delivery system of claim 15, wherein the medicament delivery system further comprises a medicament cartridge containing medicament.

19. A method of operating a medicament delivery system that comprises a hold assistance device and a medicament delivery device,
wherein the hold assistance device comprises a body comprising:
a receiving volume for receiving the medicament delivery device;
a proximal portion comprising a proximal end of the body;
a distal portion comprising a distal end of the body, the proximal end and the distal end defining an axial direction; and
a connecting portion arranged between the proximal portion and the distal portion, wherein the connecting portion is configured to flex into the receiving volume in a direction generally normal to the axial direction, causing the proximal portion to move axially relative to the distal portion, wherein the medicament delivery device comprises:
a main body configured to receive a medicament cartridge and comprising a proximal end and a distal end;
a needle for delivery of medicament from the medicament cartridge;
a needle cover axially movable relative to the main body between:
an extended position in which the needle cover extends from the distal end of the main body and covers a distal end of the needle which protrudes from the main body; and a retracted position in which the needle cover is arranged in a proximal position relative to the extended position such that the distal end of the needle protrudes from a distal end of the needle cover; and
a needle cover biasing member configured to bias the needle cover axially in a distal direction towards the extended position,
wherein the distal portion of the body of the hold assistance device is configured to be coupled to the main body of the medicament delivery device, and the proximal portion of the body of the hold assistance device is configured to be movable relative to the main body of the medicament delivery device along the axial direction, and
wherein when the hold assistance device is coupled to the medicament delivery device and the connecting portion is in a flexed state, the connecting portion is arranged to resist axial movement of the needle cover, and
wherein the method comprises:
coupling the distal portion of the body of the hold assistance device to the main body of the medicament delivery device;
moving the needle cover from the extended position to the retracted position;
moving the body of the hold assistance device from a first position in which the connecting portion is in an unflexed state into a second position in which the connecting portion is in a flexed state and is arranged to protrude into the receiving volume, such that the connecting portion is arranged to resist an axial movement of the needle cover from the retracted position to the extended position; and
moving the body of the hold assistance device from the second position to the first position to cause the connecting portion to unflex such that it no longer protrudes into the receiving volume and the needle cover is free to move axially in the distal direction towards the extended position under a biasing force of the needle cover biasing member.

* * * * *